(12) United States Patent
Hwang et al.

(10) Patent No.: US 7,795,498 B2
(45) Date of Patent: Sep. 14, 2010

(54) USE OF ATBG1 GENE FOR THE GENERATION OF TRANSGENIC PLANTS WITH INCREASED RESISTANCE TO VARIOUS ABIOTIC STRESS

(75) Inventors: Inhwan Hwang, Gyeongsangbuk-do (KR); Kwang Hee Lee, Kyeongsangnam-do (KR)

(73) Assignees: Postech Foundation, Gyeongsangbuk-do (KR); FNP Co., Ltd., Gyeonggi-do (KR)

( * ) Notice: Subject to any disclaimer, the term of this patent is extended or adjusted under 35 U.S.C. 154(b) by 413 days.

(21) Appl. No.: 11/722,578

(22) PCT Filed: Dec. 22, 2005

(86) PCT No.: PCT/KR2005/004482
§ 371 (c)(1),
(2), (4) Date: Jun. 22, 2007

(87) PCT Pub. No.: WO2006/068442
PCT Pub. Date: Jun. 29, 2006

(65) Prior Publication Data
US 2009/0138983 A1    May 28, 2009

(30) Foreign Application Priority Data
Dec. 22, 2004  (KR) ............... 10-2004-0110730

(51) Int. Cl.
*C12N 15/82* (2006.01)
*C12N 5/14* (2006.01)
*C07H 21/04* (2006.01)

(52) U.S. Cl. .............. 800/278; 800/289; 800/298; 536/23.6; 435/419; 435/468

(58) Field of Classification Search .............. None
See application file for complete search history.

(56) References Cited

U.S. PATENT DOCUMENTS 6,495,742 B1 *  12/2002  Shinozaki et al. ........... 800/298
7,368,632 B2 *  5/2008  Robertson et al. .......... 800/295

OTHER PUBLICATIONS

Piao et al., Database GenEmbl, Accession No. AF183827, Jan. 1, 2000. See office action.*
Cheuk et al., Accession No. BT000515, Sep. 25, 2002. See office action.*
Glenn Thorlby, et al., Title: the Sensitive to Freezing2 Gene . . . , The Plant Cell, vol. 16, pp. 2192-2203, 2004.
Karl-Josef Dietz et al., Title: Extracellular B-glucosidase activity in . . . , Journal of Experimental Botany, vol. 51, No. 346, pp. 937-944, 2000.

* cited by examiner

*Primary Examiner*—Eileen B O Hara
(74) *Attorney, Agent, or Firm*—Lucas & Mercanti, LLP

(57) ABSTRACT

The present invention relates to a use of AtBG1 {*Arabidopsis thaliana* β-glucosidase 1) gene and a transgenic plan with the AtBG1 gene insertion, more precisely, a use of AtBG1 gene for the generation of a transgenic plant having resistance to various environmental stresses by increasing the level of abscisic acid (ABA), a kind of plant hormone, and a transgenic plant having stress-resistance with the AtBG1 gene insertion. Plants have enhanced resistance against various environmental stresses including low temperature, salt damage and dehydration owing to the increased level of ABA. Thus, the method to increase the level of ABA can greatly contribute to the enhancement of agricultural production.

7 Claims, 21 Drawing Sheets

FIG. 1

```
AtBG1      MVRFEKVHLVLGLALVLTLVGAPTKAQGPVCGAGLPDKFSRLNFPEGFIWGTATAAFQV-EG    60
Atpsr3.1   MVLQKLPLIGLLLLLTIVAS--PANADGPVCPPS--NKLSRASFPEGFLFGTATAAYQVPRF
AtGLuc     MALKAILFLGLFLVVIVSPI---TVYGQAVCPAS--STFGRGSFPDGFLFGATTSAFQH-EG
Myrosin    LPSSSPQSSKRRCNLSFTTRSARVGSQNGVQMLSPSEIPQRDWFPSDFTFGAATSAYQI-EG AtBG1      AVNEGCRGPSMWDTFTKKFPHRCENHNAD--VAVDFYHRYKEDIQLMKDLNTDAFRLSIAWP  121
Atpsr3.1   DLMKLVRGPALWDIYCRRYPERCNNDNGD--VAVDFFHRYKEDIQLMKNLNTDAFRMSIAWP
AtGLuc     AABEGGRGSSIWDSFTLX-QHSESNNNLDGRLGVDFYHHYKEDVQLLKKINMDAFRFSISWS
Myrosin    AWNEDGKGESNWDHFCHNHPERILDGSNSD-IGANSYHMYKTDVRLLKEMGMDAYRFSISWP AtBG1      RIFPHGRMSKGINKVGVQFYHDLIDELLKNNIIPLVTVFHWDTPQDLEDEYGGFLS---GRI  181
Atpsr3.1   RIFPHGRKEKGVSQAGVQFYHDLIDELIKNGITPFVTVFHWDTPQDLEDEYGGFLS---ERI
AtGLuc     RIFPHGKKDKGVSETGVKFYNDLINELIANGVTPLVTLFQWDVPQALEDEYGGFLS---DRI
Myrosin    RILPKGTKEGGINPDGIKYYRNLINLLLENGIEPYVTIFHWDVPQALEEKYGGFLDKSHKSI AtBG1      VQDFTEYANFTFHEYGHKVKHWITFNEPWVFSRAGYDNGKKAPGRCSPYIPGYGQHCQ--DG  241
Atpsr3.1   VKDFREYADFVFQEYGGKVKHWITFNEPWVPSHAGYDVGKKAPGRSSSYV---NAKCQ--DG
AtGLuc     LEDFRDFAQFAFNKYGDRVKHWVTINEDYEFSRGGYETGEKAPGRCSKYV---NEKCV--AG
Myrosin    VEDYTYFAKVCFDNFGDKVKNWLTFNEPQTFTSFSYGTGVFAPGRCSP-----GLDCAYPTG AtBG1      RSGYEAYQVSHNLLLSHAYAVDAFRNCKQCAGGKIGIAHSPAWFEPQDL--EHVGCS----  299
Atpsr3.1   RSGYEAYLVTHNLLISHAEAVEAYRKCEKCKGGKIGIAHSPAWFEAHDLADSQDGAS----
AtGLuc     KSGHEVYTVSHNLLLAHABAVEEFRKCGKCTGGKIGIVQSPMWFEPYDK--KSTSSPSEEI
Myrosin    NSLVEPYTAGHNILLAHAEAVDLYNKHYKRDDTRIGLAFDVMGRVPYGT--SFLDKQ---A AtBG1      IERVLDFILGWHLAPTTYGDYPQSMKDRVGHRLPKFTEAEKKLLKGSTDYVGMNYYTSVP-  360
Atpsr3.1   IDRALDFILGWHLDTTTFGDYPQIMKDIVGHRLPKFTTEQKAKLKASTDFVGLNYYTSVF-
AtGLuc     VKRAMDFTLGWHMEPITHGDYPQAMKDVVGSRLPSFTPEQKEKLKGSYDFVGINYFTSTFV
Myrosin    EERSWDINLGWFLEDVVRGDYPFSMRSLAEERLPFFKDEQKEKLACSYNMLGLNYYTSRP- AtBG1      AKEIS-PDPK-SPSWTT-DSLVDWDSKSVDGYKIGSKPFNGKLDVYSKGLRYLLKYIKDNY  420
Atpsr3.1   SNHLEKPDPS-KPRWMQ-DSLITWESKNAQNYAIGSKPLTAALNVYSRGFRSLLKYIKDKY
AtGLuc     AHTDN-VNPE-KPSWEA-DSRLQLHSNNVDGFKIGSQPATAKYPVCADGLRKVLKYIKENY
Myrosin    SKNID-ISPNYSPVLNTDDAYASQEVNGPDGKPIGPPMGNPWIYMYPEGLKDLLMIMKNKY AtBG1      GDPEVIIAENGYGE-DLGEKHNDVNFGTQDHNRKYYIQRHLLSMHDAICKDKVNVTGYFVW  480
Atpsr3.1   ANPEIMIMENGYGE-ELGAS-DSVAVGTADHNRKYYLQRHLLSMQEAVCIDKVNVTGYFVW
AtGLuc     NDPEIIVTGNGYKE-TLEEK-DVLPDALSDSNRKYYHMRHLMALHGAVCEDKVNVKCYFVS
Myrosina   GNPPIYITENGIGDVDTKETPLPMEAALNDYKRLDYIQRHIATLKESIDLGS-NVQGYFAW AtBG1      SLMDNFEWQDGYKARFGLYYIDFQNNLTRHQKVSGKWYSEFLKPQFPTSKL-REEL       528
Atpsr3.1   SLLDNFEWQDGYKNRFGLYYVDFKNNLTRYEKESGKYYKDFLSQGVRPSALKKDEL
AtGLuc     SLMDGLEWEDGYKTRSGLYYVDYGHNMGRHEKQSAKWLSKLLEKVPDTIQSKVDSDSRKEL
Myrosin    SLLDNFEWFAGFTERYGIVYVDRNNNCTRYMKESAKWLKEFNTAKKPSKKILTPA
```

USE OF ATBG1 GENE FOR THE GENERATION OF TRANSGENIC PLANTS WITH INCREASED RESISTANCE TO VARIOUS ABIOTIC STRESS

CROSS-REFERENCE TO RELATED APPLICATIONS

This application is a 371 of PCT/KR2005/004482 filed on Dec. 22, 2005, which claims the benefit of Korean Patent Application No. 10-2004-0110730 filed on Dec. 22, 2004, the contents of each of which are incorporated herein by reference.

TECHNICAL FIELD

The present invention relates to a use of AtBG1 (*Arabidopsis thaliana* β-glucosidase 1) gene and a transgenic plant with the AtBG1 gene insertion, more precisely, a use of AtBG1 gene for the generation of a transgenic plant having resistance to various environmental stresses by increasing the level of abscisic acid (ABA), a kind of plant hormone, and a transgenic plant having stress-resistance with the AtBG1 gene insertion.

BACKGROUND ART

The phytohormone, abscisic acid (ABA) plays critical roles in physiological processes including seed dormancy, germination and adaptive responses to environmental stresses (Finkelstein R. R. et al., *Plant Cell* 14: 515, 2002; J. K. Zhu. *Annu Rev Plant Biol.* 53: 247, 2002; Zeevaart J. A. D. and Creelman R. A., *Ann. Rev. Plant Physiol. Plant Mol. Biol.* 39: 439, 1988; Leung J. and Giraudat J. *Annu Rev Plant Physiol Plant Mol Biol.* 49: 199, 1998). ABA was found almost at the same time by two study groups; F. T. Addincott and P. F. Wareing. F. T. Addincott group, studying on the falling of unripe fruits, isolated abscis II as a stimulator of dropping leaves from cotton fruits. And the other study group of P. F. Wareing, studying on winter dormancy of tree buds, isolated an inducer of dormancy from Betula Pubescence, a member of birch, and then named it dormin. In 1965, dormin and abscis II were confirmed to be identical, then, they began to be called abscisic acid (referred as 'ABA' hereinafter).

Dormant seeds, tree buds and bulbs contain a huge amount of ABA and the content of ABA decreases as they are germinated. ABA is also involved in stomatal movement. Precisely, when a plant is dehydrated, ABA synthesis is accelerated and pores of a leaf are closed thereby, resulting in the protection a plant from water loss. For example, a transgenic tomato plant named flacca showed no stomatal closure because of low levels of ABA, compared with that in a wild type plant.

Cellular ABA levels fluctuate constantly to allow plants to adjust to the changing physiological and environmental conditions. In particular, cellular ABA levels are controlled by equilibrium between biosynthesis and degradation. De novo protein synthesis is essential to increase the cellular ABA level. In the meantime, ABA level decreases by degradation of ABA resulted from oxidation or conjugation into inactive forms (Zeevaart J. A. D. and R. A. Creelman, *Ann. Rev. Plant Physiol. Plant Mol. Biol.*, 39: 439, 1988; Leung J. and Giraudat J., *Annu Rev Plant Physiol Plant Mol Biol.* 49: 199, 1998; Cutler A. J. and Krochko J. E., *Trends in Plant Science* 4: 472, 1999; Qin X. and Zeevaart J. A., *Proc. Natl. Acad. Sci. USA.* 96: 15354, 1999).

Low levels of ABA result in a variety of physiological defects including precocious germination, wilting and sensitivity to environmental stress (Cutler A. J. and Krochko J. E., *Trends in Plant Science* 4: 472, 1999; Koornneef M. et al., *Theor. Appl. Genet.* 61: 385, 1982; Rock C. D. and Zeevaart J. A., *Proc. Natl. Acad. Sci. USA.* 88: 7496, 1991), which indicates that controlling ABA levels properly by equilibrium between synthesis and degradation is very important for various physiological responses. The cellular ABA content is lowered via two pathways. The first pathway is hydroxylation of ABA at the 8' position by cytochrome P470 CYC707A to form unstable 8'-hydroxy ABA. This unstable intermediate is subsequently converted to phaseic acid by spontaneous isomerization (Zeevaart J. A. D. and Creelman R. A., *Ann. Rev. Plant Physiol.* 39; 439, 1988; T. Kushiro, et al., *EMBO J.* 23: 1647, 2000)

The other pathway lowering cellular ABA content is conjugation with glucose which is mediated by glucosyltransferase, thereby ABA glucose ester (ABA-GE) is generated (Cutler A. J. and Krochko J. E., *Trends in Plant Science* 4: 472, 1999; Walton D. C. and Li Y., in *Plant Hormones: Physiology, Biochemistry and Molecular Biology*, 140-157; Xu Z. J. et al., *Plant Physiol.* 129: 1285, 2002). Conjugated ABA-GEs are stored in vacuoles or apoplastic space (Kaiser W. et al., *J. Plant Physiology* 119: 237, 1985; Dietz K. J. et al., *J. Exp. Botany* 51: 937, 2000). However, the issue of whether biologically inactive ABA-GEs constitute a reserved or stored form of ABA remains to be clarified.

In the present invention, the inventors confirmed that AtBG1, an *Arabidopsis* β-glucosidase homolog localized to the ER, displays ABA-GE hydrolyzing activity, and increases the cellular ABA content through rapid polymerization of lower molecular weight AtBG1 into higher molecular weight forms under conditions of dehydration stress. A mutant *Arabidopsis thaliana* (referred as 'mutant atbg1' hereinafter) with a T-DNA insertion in AtBG1 displayed a reduced ABA level, defective stomatal closure, a yellow leaf phenotype due to the lack of chloroplast and sensitive response to abiotic stress. On the other hand, a mutant *Arabidopsis thaliana* over-expressing the AtBG1 gene displayed 2.5-fold higher ABA level and stronger resistance to environmental stress than those of control.

The present inventors, therefore, completed this invention by confirming that the AtBG1 gene can be a great asset to a plant having a strong resistance to various environmental stresses including salt damage, cold damage and dehydration.

DISCLOSURE

Technical Problem

It is an object of the present invention to provide a method for the generation of a transgenic plant having a strong resistance to various environmental stresses.

Technical Solution

In order to achieve the above object, the present invention provides a use of a gene encoding AtBG1 (*Arabidopsis thaliana* β-glucosidase 1) increasing resistance to environmental stress in a plant or its variant.

The present invention also provides a transgenic plant having resistance to environmental stress with the insertion of a gene encoding AtBG1 or its variant.

The present invention further provides a method for the generation of a plant having resistance to environmental stress by increasing the level of ABA in the plant.

The present invention also provides a method to increase resistance to stress in a plant by inserting the AtBG1 gene or AtBG1 protein.

Hereinafter, the present invention is described in detail.

The present invention provides a use of a gene encoding AtBG1 (*Arabidopsis thaliana* β-glucosidase 1) increasing resistance to environmental stress in a plant or its variant.

The phytohormone, abscisic acid (ABA), plays an important role in a variety of physiological processes including seed dormancy, germination and adaptive responses to environmental stress conditions. The lower level of cellular ABA results in various phenotypes such as precocious germination or wilting. The cellular ABA content is lowered by such pathway as conjugation with glucose, which is converted into inactive ABA glucose ester (ABA-GE) by glucosyltransferase. In the present invention, it was confirmed that AtBG1, β-glucosidase homolog isolated from *Arabidopsis thaliana*, could increase ABA levels by converting ABA-GE into ABA, which results in enhanced resistance to environmental stress in a plant. The environmental stress includes high temperature, salt damage, dryness, pollution, pathogen, wound, low temperature, excessive light condition, ozone, herbicide, excessive exposure on UV and osmotic shock.

To determine expression pattern of the AtBG1 gene under various environmental stresses, stresses such as high concentration of NaCl, low temperature and dehydration were given to *Arabidopsis thaliana*, followed by observation on expression of AtBG1. As a result, AtBG1 expression was induced by NaCl stress in a wild-type plant, while Gluc and psr3.1 gene encoding other β-glucosidase homologs expressions were not induced (FIG. 2). The results indicate that the AtBG1 gene only, among β-glucosidase homologs, increases stress-resistance in a plant.

Indirect investigation was also performed to confirm whether AtBG1 can increase resistance to environmental stresses in a plant. A phenotype of a mutant line with a T-DNA insertion in AtBG1 'mutant atbg1' was observed. Unlike a wild type, the mutant displayed a yellow leaf and was short in height (FIG. 9 and FIG. 10). In wild type plants, pores are open during the day and closed during the night. However, in the 'mutant atbg1', stomatal closure was not observed even during the night (FIG. 13). Under the dry condition, water loss was 1.5-fold higher in the mutant than in a wild type (FIG. 15) and dehydration level was also higher, displaying wiltering of most leaves (FIG. 16).

From the results, it was confirmed that resistance to environmental stresses is weakened in the 'mutant atbg1' owing to the lack of AtBG1 protein.

The present inventors insert the AtBG1 gene into the 'mutant atbg1', resulting in the construction of another transgenic *Arabidopsis thaliana* plant line (referred as 'rescued atbg1' hereinafter). The experiment was performed by the same manner as described in the experiment with the 'mutant atbg1' to determine whether the phenotype of the 'mutant atbg1' was resulted from the mutation in the AtBG1 gene or not.

As a result, 'rescued atbg1' displayed clear green color after 1 week (1w), 2 weeks (2w) (FIG. 9) and 4 weeks (4w) (FIG. 10) from germination, similarly to a wild type, was tall in height and displayed normal stomatal action (that is, pores were open during the day and closed during the night, like a wild type) (FIG. 13). Water loss under dehydration was less than in wild type (FIG. 15). After 21-day of culture under dehydration condition, it was observed that the 'rescued abtg1' was growing normally without displaying darkish leaves by dehydration (FIG. 16).

From the results, it was confirmed that the change of phenotype of the 'mutant abtg1' was resulted from the mutation in the AtBG1 gene.

AtBG1 protein encoded by the AtBG1 gene increases the level of abscisic acid in a plant, and increases resistance to environmental stresses thereby.

In a preferred embodiment of the present invention, it was examined whether AtBG1 protein could hydrolyze ABA-GE generated by ABA glucosyltransferase. Wild type AtBG1 protein and mutated AtBG1 protein with substitution or deletion mutation in the AtBG1 gene were reacted with ABA-GE (abscisic acid glucosyl ester), followed by HPLC to fractionate ABA fractions. The ABA fractions were confirmed and quantified by ELISA using an anti-ABA specific antibody. As a result, a high level of ABA was observed from the reaction of wild type AtBG1 protein and ABA-GE. On the other hand, ABA was not detected from the reaction of mutated AtBG1 protein and ABA-GE (FIG. 17 and FIG. 18). The results indicate that AtBG1 protein encoded by the AtBG1 gene increases the level of ABA by hydrolyzing ABA-GE.

A yellow leaf of 'mutant atbg1' turned into normal green by the insertion of AtBG1 (FIG. 12) and stomatal closure at night was also induced by the AtBG1 insertion (FIG. 14). Those results also support that ABA production by AtBG1 contributes to stress-resistance in a plant.

The other confirmed result that AtBG1 localizes to the ER which is an intracellular organelle (FIG. 23-FIG. 26).

The present invention, thus, provides a use of the AtBG1 gene increasing resistance to environmental stress in a plant and its homologous gene in another plant. The gene of the present invention can be inserted into a plant independently or using a vector according to the conventional plant transfection method. For example, *Agrobacterium* mediated method, gene gun, PEG method and electroporation, which are well-known to those in the art, are available.

A variant means a protein in which some of amino acids in amino acid sequence of AtBG1 are mutated but has no functional changes. The variant includes natural or artificial mutants that have similar structural and physiological functions to AtBG1 protein homolog.

The present invention also provides a transgenic plant having stress-resistance by the insertion of a gene encoding AtBG1 or its variant.

To produce a transgenic plant having resistance to environmental stress, the present inventors constructed a plant expression vector 'pBI121::AtBG1' harboring the AtBG1 gene and transfected *Agrobacterium* (LBA4404) with the vector, which was deposited at Korean Collection for Type Cultures (KCTC) of Korea Research Institute of Bioscience and Biotechnology (KRIBB), on Nov. 18, 2004 (Accession No: KCTC 10729BP).

A transgenic plant was generated by transfecting *Arabidopsis thaliana* with the *Agrobacterium* transformed with the above vector 'pBI121::AtBG1' by the floral dip method.

Environmental stress-dependent phenotypes of the transgenic *Arabidopsis thaliana* containing the AtBG1 gene were observed. As a result, the wild type was wilted by high level of NaCl, but AtBG1 transgenic *Arabidopsis thaliana* was growing normally (FIG. 4). While the root growth rate of the wild type was reduced with increasing NaCl concentration, the root growth rate of transgenic *Arabidopsis thaliana* was increased with increasing NaCl concentration to the fixed content (FIG. 5).

The above results indicate that a transgenic plant with the AtBG1 insertion displays resistance to environmental stress such as high concentration of NaCl.

Another transgenic plant containing a gene encoding AtBG1 or its variant can also be included in the present invention.

It is also understood that the present invention includes an off-spring or a cloned plant of a transgenic plant showing resistance to environmental stress by AtBG1 insertion and seeds, fruits, ears, tubers, tuberous roots, trees, callus or protoplasts of the plant.

The present invention further provides a method for the generation of a plant having resistance to environmental stress by increasing the level of cellular ABA.

The method above comprises the following steps:

i) inserting the AtBG1 gene/homologous gene of another plant or a vector containing the gene into a plant; and ii) redifferentiating the plant cells by tissue culture.

The present inventors transfected *Agrobacterium* with pBI121::AtBG1 vector containing the AtBG1 gene, which would be used to transform *Arabidopsis thaliana* by the floral dip method, resulting in the generation of a transgenic plant. The transgenic plant displayed resistance to various stress conditions owing to the increased level of free ABA resulted from the expression of the AtBG1 gene.

The present invention also provides a method for the generation of a stress-resistant transgenic plant with the AtBG1 gene or AtBG1 protein insertion.

As described hereinbefore, AtBG1 converts abscisic acid glucose ester (ABA-GE) into abscisic acid (ABA) by hydrolysis, and the increased level of ABA increases resistance to stress conditions in a plant, which are promoted by AtBG1 polymerization.

Under dehydration condition, AtBG1 over-expressing plant displayed increased ABA contents owing to the activation of AtBG1 (see FIG. 27-FIG. 31) and under normal growth condition, ABA-GE was converted into ABA by AtBG1 polymerization to regulate the diurnal increment of ABA (see FIG. 32-FIG. 34 and FIG. 36-FIG. 38). The results indicate that not a signal transduction pathway but AtBG1 contributes to increase in the active pool of cellular ABA. Unlike de novo biosynthesis which is rather complicated and time-consuming effort, ABA production by AtBG1-mediated ABA-GE hydrolysis is simple and easy, enabling the quick regulation of the active ABA pool according to stress conditions and duration. Thus, it was judged that the way to increase cellular ABA contents from ABA-GE is to resist against dehydration stress in a plant.

DESCRIPTION OF DRAWINGS

The application of the preferred embodiments of the present invention is best understood with reference to the accompanying drawings, wherein:

FIG. 1 is a diagram showing the comparison of amino acid sequences between AtBG1 (*Arabidopsis thaliana* β-glucosidase 1) and other β-glucosidase homologs, FIG. 2-FIG. 6 describe that environmental stresses induce AtBG1 expression and a transgenic plant harboring the AtBG1 gene shows increased resistance to NaCl stress.

FIG. 8 is a gel electrophoresis photograph confirming by RT-PCR using AtBG1 gene-specific primers that 'mutant atbg1' does not contain AtBG1 transcript, FIG. 9 and FIG. 10 are photographs taken one (1 W), two (2 W) and four (4 W) weeks after germination of each wild type, 'mutant atbg1' and 'rescued atbg1', FIG. 11 is a photograph showing AtBG1::HA expression in 'rescued atbg1' which was confirmed by Western blot analysis using anti-HA antibody (Roche), FIG. 12 is a set of photographs showing the recovery of phenotype of 'mutant atbg1' similarly to that of the wild type by AtBG1 insertion, FIG. 13 is a graph showing the pore sizes of leaves of *Arabidopsis thaliana* cultured under the light/dark cycle of 16/8 hours, measured day and night (n=150, bar=standard error), FIG. 14 is a graph showing the pore sizes of leaves of 'mutant atbg1', measured day and night after inserting ABA or treating NAME inhibiting NO synthase activity during stomatal closure (n=200, bar=standard error), FIG. 15 is a graph showing the results of weighing leaves standing at 20° C. under 10% relative humidity, a dehydration condition, for the indicated time period, for the comparison of water loss, FIG. 16 is a set of photographs showing the results of culture of wild type, 'mutant atbg1' and 'rescued atbg1' for 14 days (14d) or 21 days (21d) under dehydration condition, FIG. 17 is a photograph showing the results of immunopurification using anti-HA antibody in protoplasts of wild type plants transformed with AtBG1:HA, AtBG1 [E207Q], AtBG1 [AC105] and empty vector, FIG. 18 is a set of graphs showing the results of HPLC of reaction products produced by immunopurified AtBG1:HA protein in the presence of ABA-GE in a proper buffer solution, FIG. 19 is a graph showing the result of ELISA with ABA fractions of HPLC using anti-ABA antibody, FIG. 20 is a graph showing the result of ELISA using anti-ABA antibody (Agdia) measuring the levels of ABA in wild type, 'mutant atbg1' and 'rescued atbg1' seeds, FIG. 21 is an photograph of western blot analysis showing the level of AtBG1:HA in 'rescued atbg1', confirmed by using anti-HA antibody, FIG. 22 is a graph showing the results of germination assays of wild type, 'mutant atbg1' and 'rescued atbg1', FIG. 23 is a schematic diagram showing the structure of GFP tagged AtBG1 gene, FIG. 24 is a set of fluorescent photomicrographs showing the ER by using Bip:RFP as an ER marker and GFP as a cytosolic soluble protein, FIG. 25 is a set of fluorescent photomicrographs showing the intracellular locations of AtBG1:HA and BiP:REP, FIG. 26 is a photograph showing that a protein extract obtained from protoplasts transformed with AtBG1:HA but not treated with tunicamycin was treated with endo-H and PNGase F, preparing a test sample, and a protein extract obtained from protoplasts transformed with AtBG1:HA and treated with tunicamycin was analyzed by blotting, FIG. 27 is a graph showing the ABA-GE hydrolyzing activity of microsomal fractions obtained from 'rescued atbg1' treated or not-treated with dehydration, FIG. 28 is a set of photographs showing AtBG1 polymerization under dehydration stress, FIG. 29 is a graph showing the ABA-GE hydrolyzing activity of high molecular AtBG1, FIG. 30 and FIG. 31 are photographs and a graph showing the formation of high molecular AtBG1, FIG. 32 is a graph showing the diurnal changes of ABA levels in 'rescued atbg1', FIG. 33 is a set of photographs showing the results of one-day detection of AtBG1 in protein extracts obtained from 'rescued atbg1', FIG. 34 is a graph showing the results of quantifying AtBG1 in high molecular weight form, FIG. 36 is a set of photographs showing the result of semi-quantitative RT-PCR using primers involved in de novo biosynthesis and AtBG1, FIG. 37 and FIG. 38 are graphs showing the time-dependent expression levels.

MODE FOR INVENTION

Figure 2:
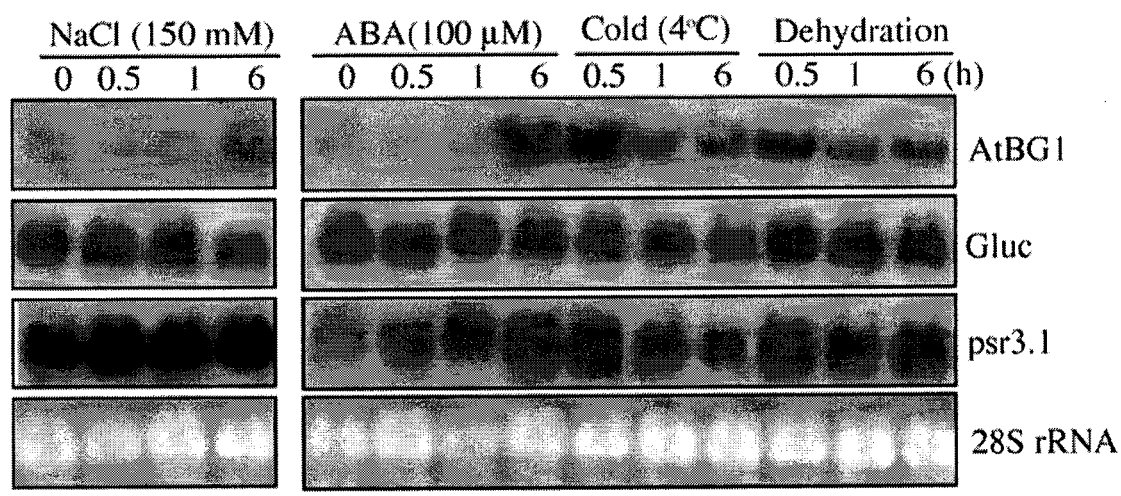
FIG. 2 is a set of electrophoresis photographs showing the results of Northern blot analysis using cDNAs of AtBG1, AtGluc (AF082157) and Atpsr3.1 (U72153) as probes, for which 'wild type' *Arabidopsis thaliana* was received various chemical stresses (low temperature, dehydration, high concentration of NaCl) for 30 min, 1 h or 6 h and then total RNA was extracted.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Transgenic *Arabidopsis thaliana*

<1-1> AtBG1 Gene Isolation from cDNA Library

The present inventors obtained 'subtraction cDNA library' (Pih K. T. et al., *Mol. Cells*, 7: 567, 1997) containing genes whose expressions are induced by high concentration of NaCl, one of osmotic stresses. From the library, AtBG1, an *Arabidopsis thaliana* gene encoding one of β-glucosidase homologs (FIG. 1), was isolated. PCR was performed with a forward primer represented by SEQ. ID. No 1 and a reverse primer represented by SEQ. ID. No 2 by using DNA polymerase (Taq polymerase, Takara). PCR conditions are as follows; predenaturation at 94° C. for 5 minutes, denaturation at 94° C. for 30 seconds, annealing at 50° C. for 1 second, polymerization at 72° C. for 1 minute, 50 cycles from denaturation to polymerization, and final extension at 72° C. for 10 minutes.

<1-2> Construction of Expression Vector for Plant Transformation

To generate a transgenic *Arabidopsis thaliana* transformed with AtBG1 gene, the present inventors firstly cloned AtBG1 gene into an expression vector.

Particularly, GUS site of pBI121 (Pharmacia LKB Biotechnology) having kanamycin-resistance and harboring CaMV 35S promoter was replaced with AtBG1 gene having a nucleotide sequence represented by SEQ. ID. No 3, resulting in expression vector for plant transformation 'pBI121::AtBG1'. The pBI121::AtBG1 vector was inserted into *Agrobacterium*, and the *Agrobacterium* transformant LBA4404 was deposited at Korean Collection for Type Cultures (KCTC) of Korea Research Institute of Bioscience and Biotechnology (KRIBB), on Nov. 18, 2004 (Accession No: KCTC 10729BP).

<1-3> Generation of Transgenic *Arabidopsis thaliana*

The present inventors transfected *Arabidopsis thaliana* with the expression vector harboring AtBG1 gene constructed in the above Example <1-2>.

Particularly, transfection was performed by floral dip method (Steven J. C. and Andrew F. B. The Plant Journal, 16(6): 735-743, 1998). To produce a transgenic plant, *Arabidopsis thaliana* was cultivated in MS medium and then transferred into soil. After rachis was sprouted, the sprouts of *Arabidopsis thaliana* were cut two times to prepare samples.

*Agrobacterium* transfected with pBI121::AtBG1 was cultivated in LB medium (1% tryptone, 0.5% yeast extract, 0.5% NaCl) until stationary phase, and cells were recovered by centrifugation, which were resuspended in inoculating medium (5% sucrose, 0.05% Silwet L-77 (Osi Specialties)). When OD value of the suspension reached 0.8, *Arabidopsis thaliana* sections were dipped in the suspension bottom up and stirred for 3-5 seconds smoothly. Then, *Arabidopsis thaliana* sections were transferred to a plastic tray. *Arabidopsis thaliana* sections were covered with plastic dome to keep humidity and cultured in the dark for 12-24 hours, from which a transgenic plant was obtained.

Example 2

Changes of Transgenic *Arabidopsis thaliana* by Various Stresses

<2-1> Expression of AtBG1 Gene According to Various Stresses

To examine whether the expression of AtBG1 was induced by stresses, total RNA was extracted from the wild type *Arabidopsis thaliana*. Then, environmental stresses were given to the wild type plant, followed by Northern blot analysis to measure the expression of AtBG1 gene.

Precisely, under such stress conditions as high concentration of NaCl (150 mM) and low temperature of 4° C., the plant was cultured on MS plate for 2 weeks and at that time the plate was uncovered to give dehydration stress. Total RNA was analyzed by Northern blotting by using AtBG1, Gluc (AF082157) and psr3.1 (U72153) cDNA as probes. cDNAs of Gluc (AF082157) and psr3.1 (U72153) genes, used as probes, were obtained by PCR using entire cDNA library as a template with a forward primer represented by SEQ. ID. No 4 and a reverse primer represented by SEQ. ID. No 5 and DNA polymerase (Taq polymerase, Takara). PCR conditions are as follows; predenaturation at 94° C. for 5 minutes, denaturation at 94° C. for 30 seconds, annealing at 50° C. for 1 second, polymerization at 72° C. for 1 minute, 50 cycles from denaturation to polymerization, and final extension at 72° C. for 10 minutes.

From the Northern blot analysis, it was confirmed that AtBG1 expression was induced in the wild type plant by NaCl stress but Gluc and psr3.1 expressions were not induced by environmental stress (Leah R. et al., *J Biol. Chem.* 270: 15-789, 1995; Malboobi M., and Lefebvre D. D., *Plant Mol. Biol.* 34: 57, 1997), indicating that only AtBG1 gene encoding β-glucosidase homolog was expressed (FIG. 2). That is, unlike other β-glucosidase homologs, only AtBG1 gene can increase stress-resistance of a plant.

<2-2> Phenotype of Transgenic *Arabidopsis thaliana* Under Various Stresses

The present inventors examined phenotypes of transgenic *Arabidopsis thaliana* transformed with AtBG1 gene under various environmental stresses.

Figure 3:
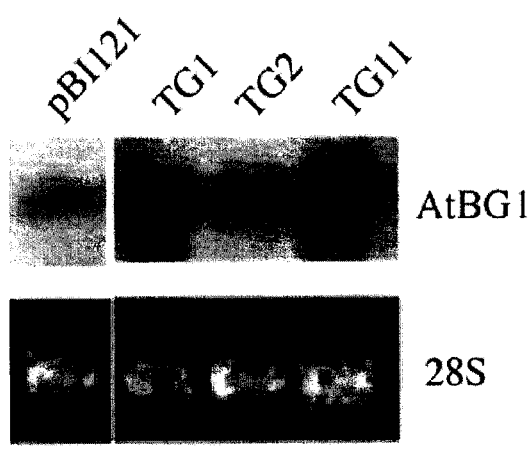
FIG. 3 is a set of gel electrophoresis photographs showing the result of Northern blot analysis with the total RNA extracted from the transgenic *Arabidopsis thaliana* transformed with the AtBG1 gene.

Particularly, total RNAs were extracted from each AtBG1 transgenic *Arabidopsis thaliana* T1 (transformant 1), T2 (transformant 2) and T3 (transformant 3) and a control *Arabidopsis thaliana* transformed with empty vector 'pBI121, followed by Northern blot analysis using AtBG1 cDNA as a probe. As a result, AtBG1 gene expressions were observed in T1, T2 and T3, except the control *Arabidopsis thaliana* transformed with empty vector (FIG. 3).

T1 was cultivated in soil for 10 days, then NaCl solution was treated to the soil every 2 hours by the concentration of 200 mM for 4 days, creating high concentration NaCl stress condition. T1 was then transferred into a fresh new MS plate. Root growth was measured 7 days after the transplantation (n=50).

Figure 4:
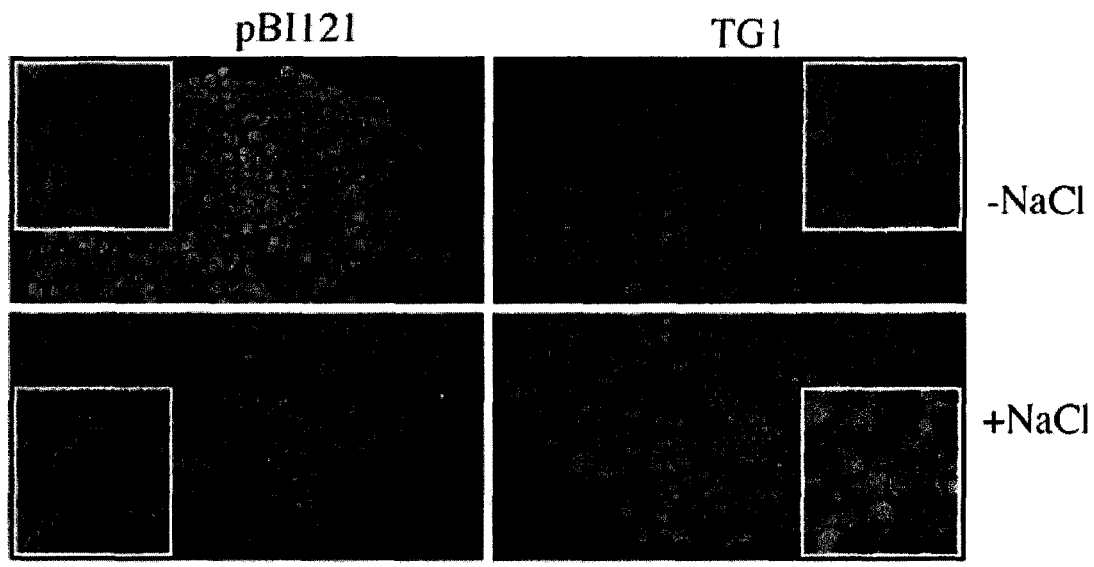
FIG. 4 is a set of photographs showing that a transgenic *Arabidopsis thaliana* transformed with the AtBG1 or empty vector pBI121 was cultured for 10 days in soil, followed by NaCl treatment for 4 days.

The *Arabidopsis thaliana* transformed with empty vector pBI121 was wilted by the high concentration of NaCl, while T1 transformed with AtBG1 displayed normal growth under the high concentration of NaCl (FIG. 4).

Figure 5:
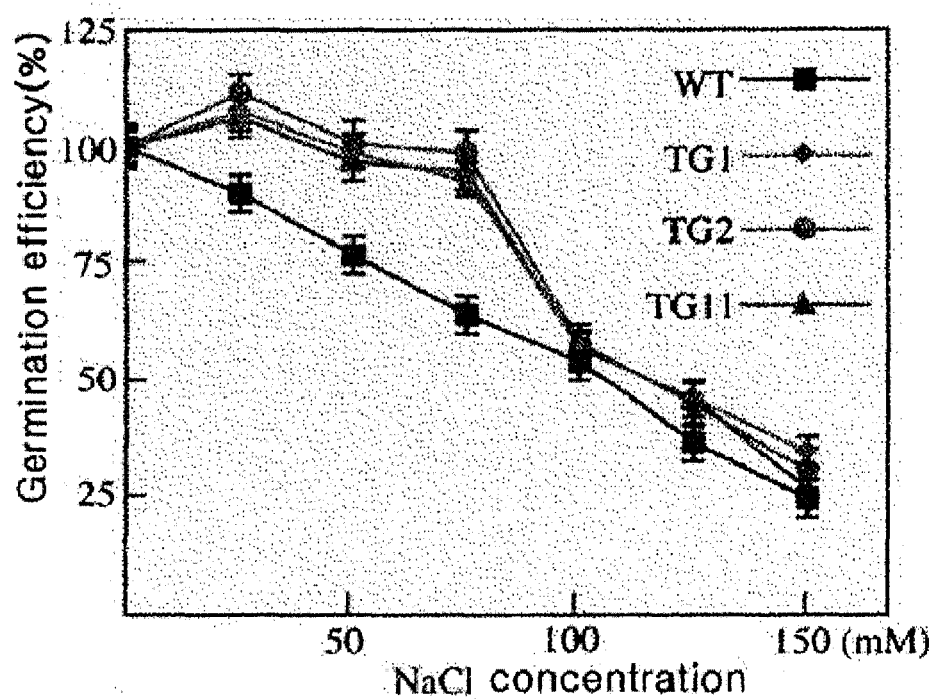
FIG. 5 is a graph showing the growth of roots of a plant which had been cultured for 4 days on MS plate and then transferred to another plate containing high concentration of NaCl (n=50)

The root growth rate in wild type which was not transformed with AtBG1 was reduced with increasing the concentration of NaCl, but the root growth rates of T1, T2 and T3 which were transformed with AtBG1 were increased with up to 100 mM of NaCl concentration (FIG. 5).

Figure 6:
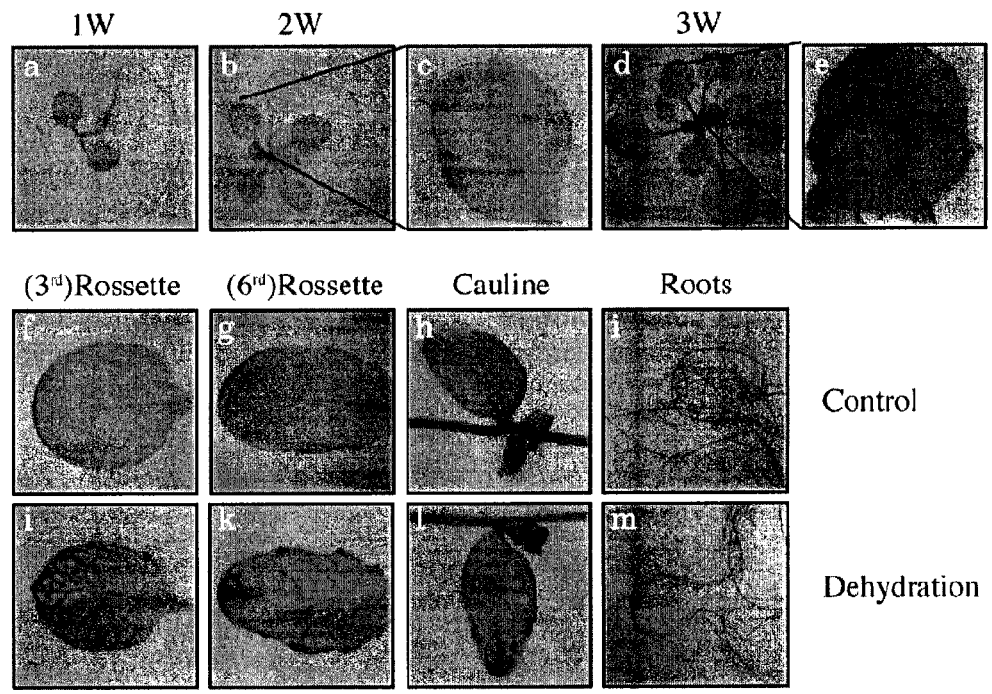
FIG. 6 is a set of photographs showing the results of X Gluc staining obtained respectively one (1 W), two (2 W) and three weeks (3 W) after the beginning of culture of a transgenic plant containing GUS under the control of the AtBG1 promoter and tissue-specific AtBG1 expression.

To further examine the expression pattern, the AtBG1 upstream region was placed in front of the β-glucosidase (GUS) coding region. Particularly, 35S promoter of 35S:GUS region of pBI121 vector was cut by a restriction enzyme and replaced by the promoter region of AtBG1 obtained by PCR. The PCR was performed with primers represented by SEQ. ID. No 9 and No 10 and DNA polymerase (Taq polymerase, Takara) by using chromosomal DNA as a template. PCR conditions are as follows; predenaturation at 94° C. for 5 minutes, denaturation at 94° C. for 30 seconds, annealing at 50° C. for 30 second, polymerization at 72° C. for 1 minute, 50 cycles from denaturation to polymerization, and final extension at 72° C. for 10 minutes. As a result, AtBG1 upstream promoter 1.7 Kb was obtained, which was then inserted into a vector. That is, the promoter region of the AtBG1 gene was tagged with GUS and inserted into a plant by the same manner as described in the above Example. GUS activity was measured by using X-Glucuronide (Rose Scientific Ltd) according to the conventional method described in a previous paper (Hwang I. and Sheen J. Nature. 413(6854): 383-9, 2001). GUS expressions in transgenic plants were very low and highly specific to hydathodes of rosettes and cauline leaves (FIG. 6). In the meantime, the transgenic plants which had been raised for 2 weeks were put in dehydration condition for 2 weeks, then GUS activity was measured by using X-Glucuronide. GUS expression deriven by the AtBG1 promoter was strongly induced in hydathodes and the vasculature of rosettes and cauline leaves, suggesting that AtBG1 participates in drought response (FIG. 6).

Example 3

Phenotype of 'Mutant Atbg1'

<3-1> Phenotype of 'Mutant atbg1'

To examine the biological function of AtBG1, the present inventors observed phenotype of 'mutant atbg1' with a T-DNA insertion in AtBG1 gene under various environmental stresses.

Figure 7A:
FIG. 7A is a schematic diagram showing a mutant line with a T-DNA insertion in AtBG1.
Figure 7B:
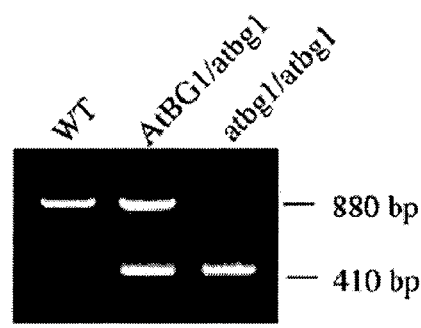
FIG. 7B is a gel electrophoresis photograph confirming whether *Arabidopsis thaliana* is mutated with a T-DNA insertion in AtBG1 by performing PCR using genomic DNA isolated from mutated *Arabidopsis thaliana* harboring a T-DNA (referred as 'mutant atbg1' hereinafter) with AtBG1 gene specific primers.

Particularly, among mutant lines with T-DNA insertions constructed at SALK institute, USA, a mutant line with a T-DNA insertion in the $9^{th}$ intron of AtBG1 gene was isolated (FIG. 7A) and the T-DNA insertion therein was confirmed. PCR was performed with a left border primer represented by SEQ. ID. No 6, a forward primer represented by SEQ. ID. No 7 and a reverse primer represented by SEQ. ID. No 8 by using DNA polymerase (Taq polymerase, Takara). PCR conditions are as follows; predenaturation at 94° C. for 5 minutes, denaturation at 94° C. for 30 seconds, annealing at 50° C. for 1 second, polymerization at 72° C. for 1 minute, 50 cycles from denaturation to polymerization, and final extension at 72° C. for 10 minutes. As a result, 410 bp PCR product was obtained and T-DNA insertion was confirmed (FIG. 7B).

Figure 8:
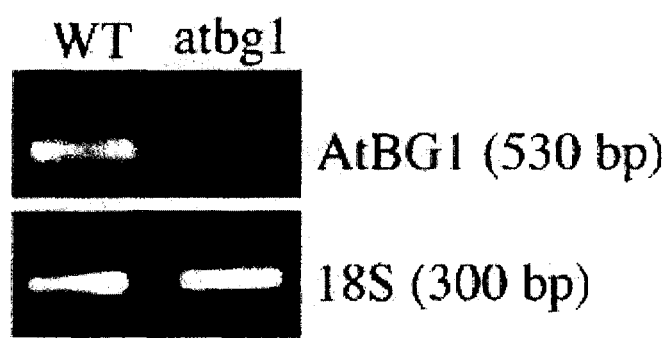
FIG. 8-FIG. 16 describe phenotypes of 'mutant atbg1' and 'rescued atbg1' whose gene loss is recovered by transfection with the AtBG1::HA gene.

The total RNA of 'mutant atbg1' was investigated by RT-PCR by using an AtBG1 specific forward primer represented by SEQ. ID. No 25 and a reverse primer represented by SEQ. ID. No 26. As shown in FIG. 8, the absence of AtBG1 mRNA was confirmed.

Figure 9:
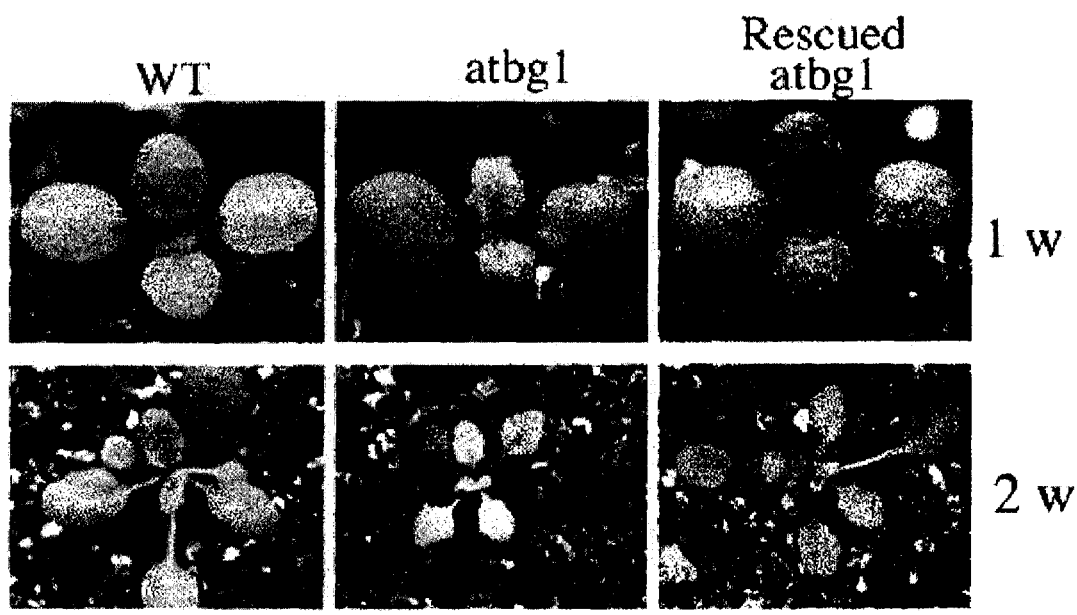
Figure 10:

Wild type and 'mutant atbg1' with a T-DNA insertion were observed 1 week (1 W), 2 weeks (2 W) (FIG. 9) and 4 weeks (4 W) (FIG. 10) after germination. As a result, the mutant plant displayed a yellow leaf and short height phenotype.

Figure 12:

Exogenous ABA was applied to one week cultivated 'mutant atbg1', followed by culture for 3 more days. The yellow leaf turned into normal green with the increase of ABA level (FIG. 12).

<3-2> Measurement of Stomatal Size of 'Mutant Atbg1'

To examine the biological function of AtBG1 in another way, the present inventors measured stomatal size of 'mutant atbg1'.

Figure 13:
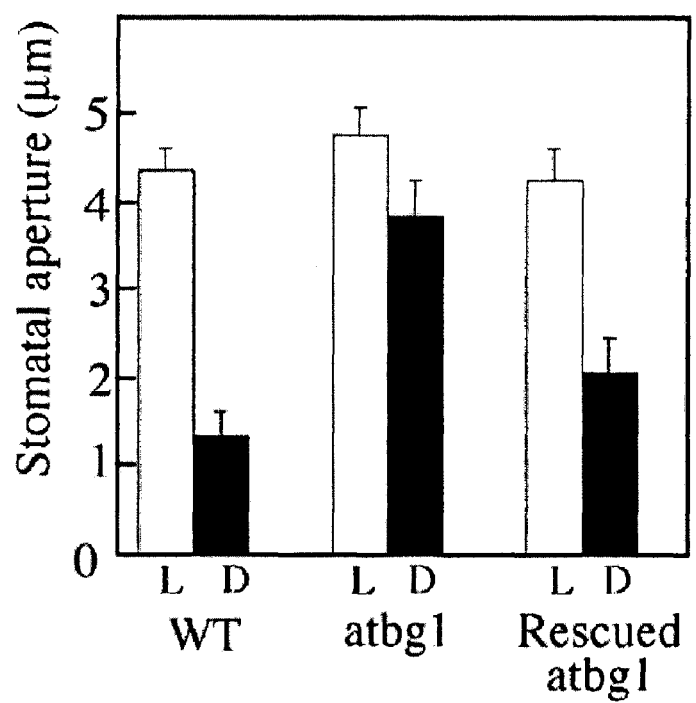

Particularly, the transgenic plant was cultured at 20° C. with 70% relative humidity under 16/8 hour-light/dark cycle and the stomatal sizes were measured at noon and midnight (n=150) (FIG. 13). In wild type plants, pores are open in the light and closed in the dark, but in the 'mutant atbg1', stomatal closure did not occur in the dark.

Figure 14:
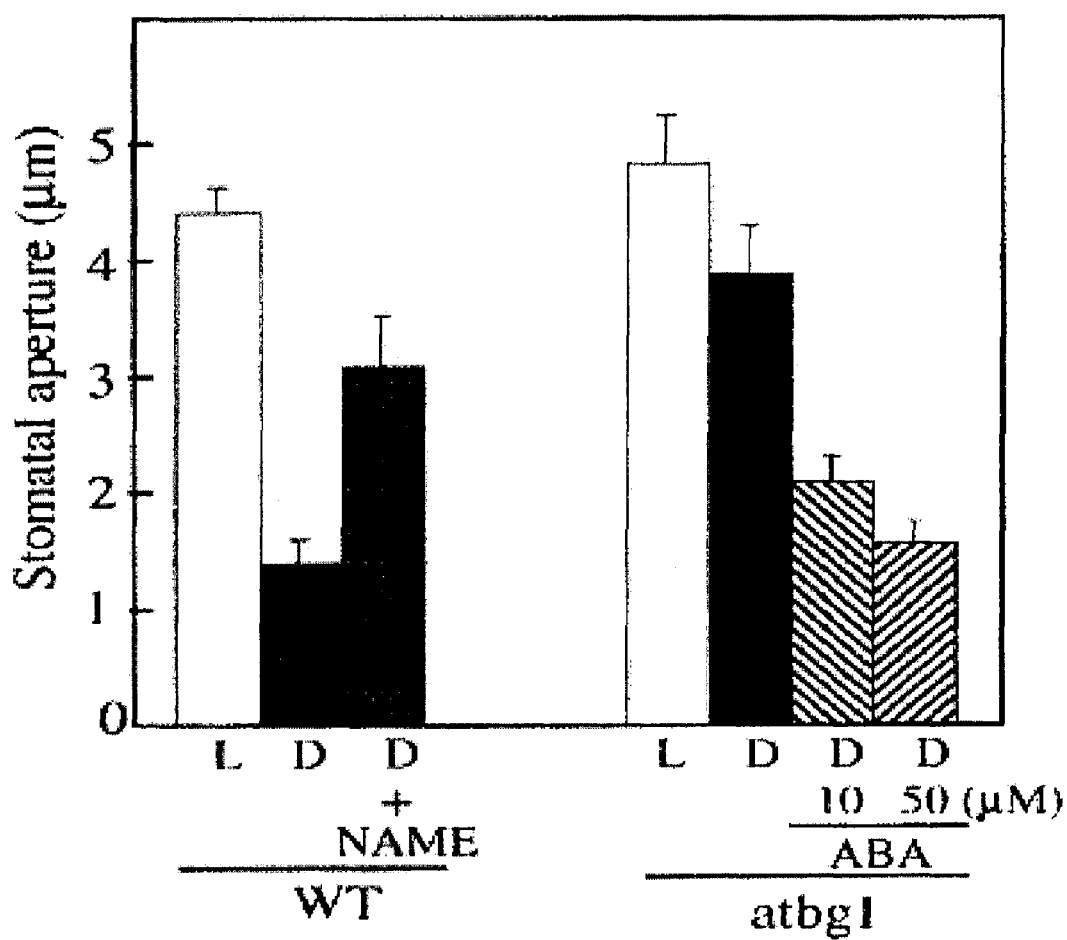

To investigate the effect of exogenous ABA on stomatal closure, the 'mutant atbg1' plant was treated with 10 μM and 50 μM of ABA at 23 o'clock and stomatal sizes were measured at 24 o'clock (FIG. 14). Control group was treated with 100 μM of NAME (L-nitroargininemethylester), known as a NO synthase, during the time of stomatal disclosure, that is for 10 hours from 4 o'clock, and stomatal sizes were measured at midnight.

The treatment of NAME to wild type results in defects in stomatal closure, and the treatment of ABA to the 'mutant atbg1' induced stomatal closure in the night, suggesting that ABA is involved in the regulation of stomatal closure in the dark (n=200, bar: standard error).

The result that the 'mutant atbg1' recovers wild type phenotype by the addition of exogenous ABA indicates that mutation in AtBG1 gene inhibits the expression of AtBG1 gene, displaying defects in ABA-mediated response.

<3-3> Phenotype of 'Mutant Atbg1' Under Dehydration Condition

To investigate the biological function of AtBG1, the present inventors observed water loss and wilting of the 'mutant atbg1' under dehydration condition.

Figure 15:
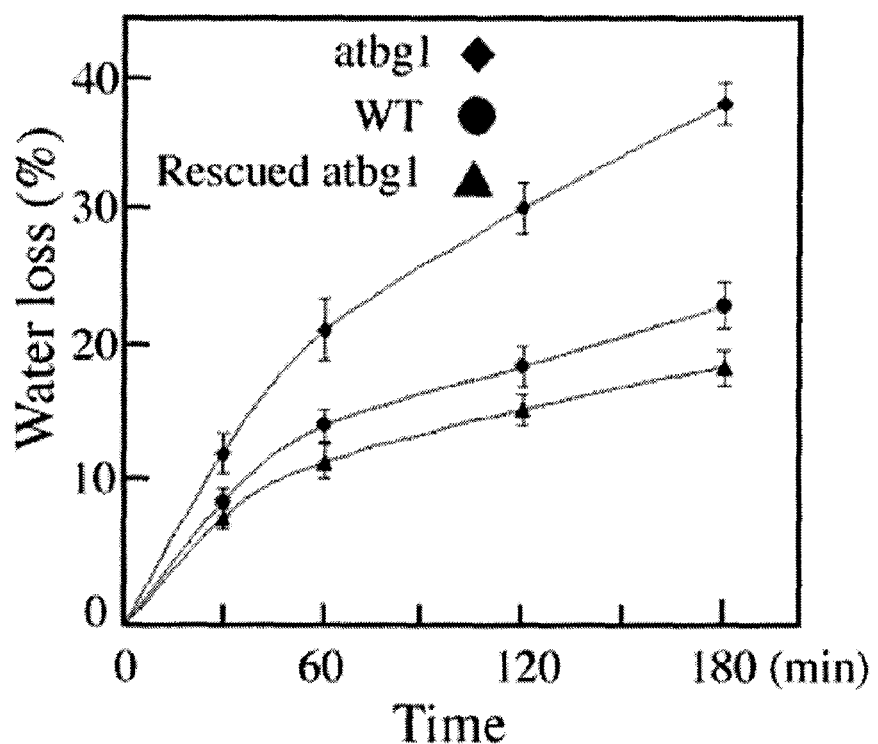

To compare water loss, leaves were left at 20° C. with 10% relative humidity (dried condition) for 3 hours, and then weights of the leaves were measured (20 rosette leaves, leaves attached on a short stem before flower buds were formed, were weighted). As a result, the 'mutant atbg1' displayed 1.5-fold higher water loss than wild type (FIG. 15).

Figure 16:
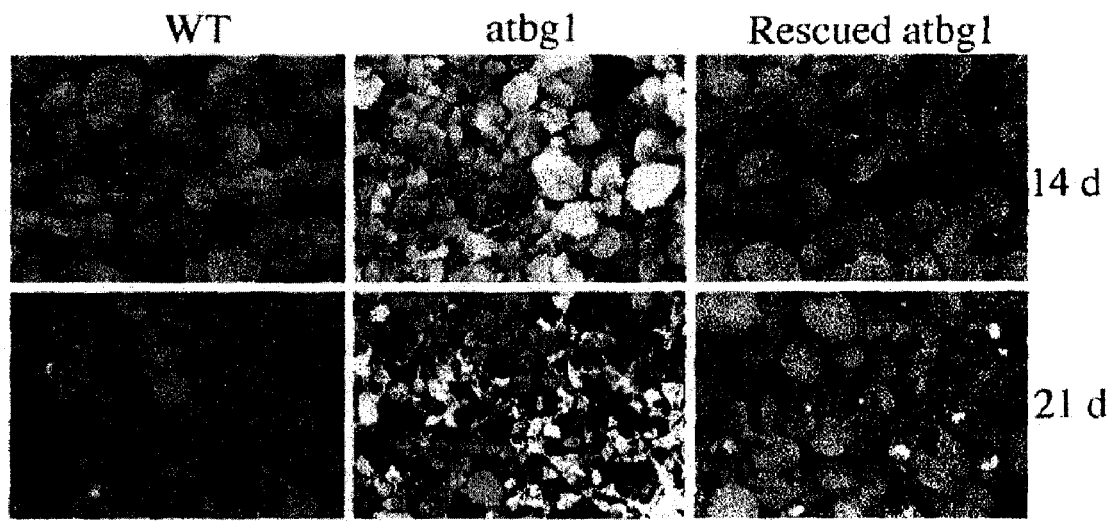

Wild type and 'mutant atbg1' were transplanted in soil in green-house and cultured at 20° C. with 70% relative humidity without providing water, respectively for 14 days (14d) and 21 days (21d). The leaf color of wild type was changed into darkish, and the leaves of the 'mutant atbg1' were suffered with serious dehydration and most of them were wilted (FIG. 16).

Thus, the 'mutant atbg1' displayed lowered resistance to environmental stresses, compared with wild type.

<3-4> Confirmation by Complementation

To confirm whether the phenotype of the 'mutant atbg1' is attributed to the mutation of AtBG1, the 'mutant atbg1' was transformed with AtBG1 gene to over-express AtBG1 gene and then experiments were performed by the same manner as described in Example 2.

Virus HA (hemagglutinin) tagged wild type AtBG1 cDNA (AtBG1::HA) was inserted into a plant to induce AtBG1 expression, resulting in complementation of mutation induced AtBG1 loss in a transformant, which was called 'rescued atbg1'.

Figure 11:
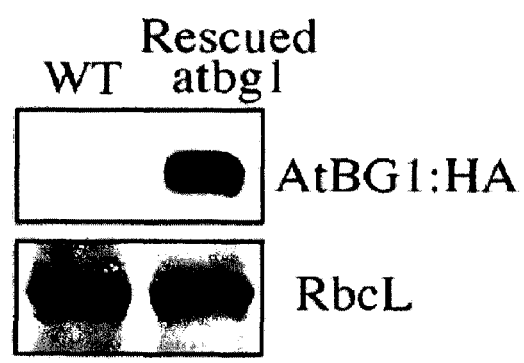

Protein extract of 'rescued atbg1' was examined by Western blot analysis using anti-HA antibody. As shown in FIG. 11, AtBG1 protein expression was confirmed.

The 'rescued atbg1' was examined by the same manner as described in Example 3. As a result, the leaves of the 'rescued atbg1' were clearly green and tall phenotype was observed, like wild type, after 1 week (1w), 2 weeks (2w) (FIG. 9) and 4 weeks (FIG. 10) after germination, and defective stomatal closure was also rescued, which means the pores were open during the day and closed during the night (FIG. 13). Under dehydration condition, water loss was less in the 'rescued atbg1' than in wild type (FIG. 15). After 21 days of culture under dehydration condition, the transformant displayed normal growth without turning into darkish leaves (FIG. 16).

From the results, it was confirmed that the phenotype of 'mutant atbg1' phenotype is attributed to the mutation of AtBG1 gene.

Example 4

ABA-GE Hydrolysis by AtBG1

<4-1> Quantification of ABA Fractions of HPLC by ELISA

The present inventors examined whether AtBG1 protein could hydrolyze ABA-GE generated by ABA glucosyltransferase (Xu Z. J. et al., *Plant Physiol.* 129: 1285, 2002).

Particularly, *Arabidopsis thaliana* was transformed with AtBG1:HA, AtBG1 [E207Q]:HA, AtBG1 [ΔC105]:HA and empty vector as a control, and protein extracts were obtained 24 hours after transformation. AtBG1[E207Q]:HA contains a substitution mutation at $207^{th}$ nucleotide, an active site of β-glycosidase (G. Davies and B. Henrissat, *Structure* 3: 853, 1995; Marana S. R. et al., *Biochim. Biophys. Acta,* 1545: 41, 2001). AtBG1[ΔC105] contains a deletion mutation that lacks 105 amino acid residues at C-terminus.

Figure 17:
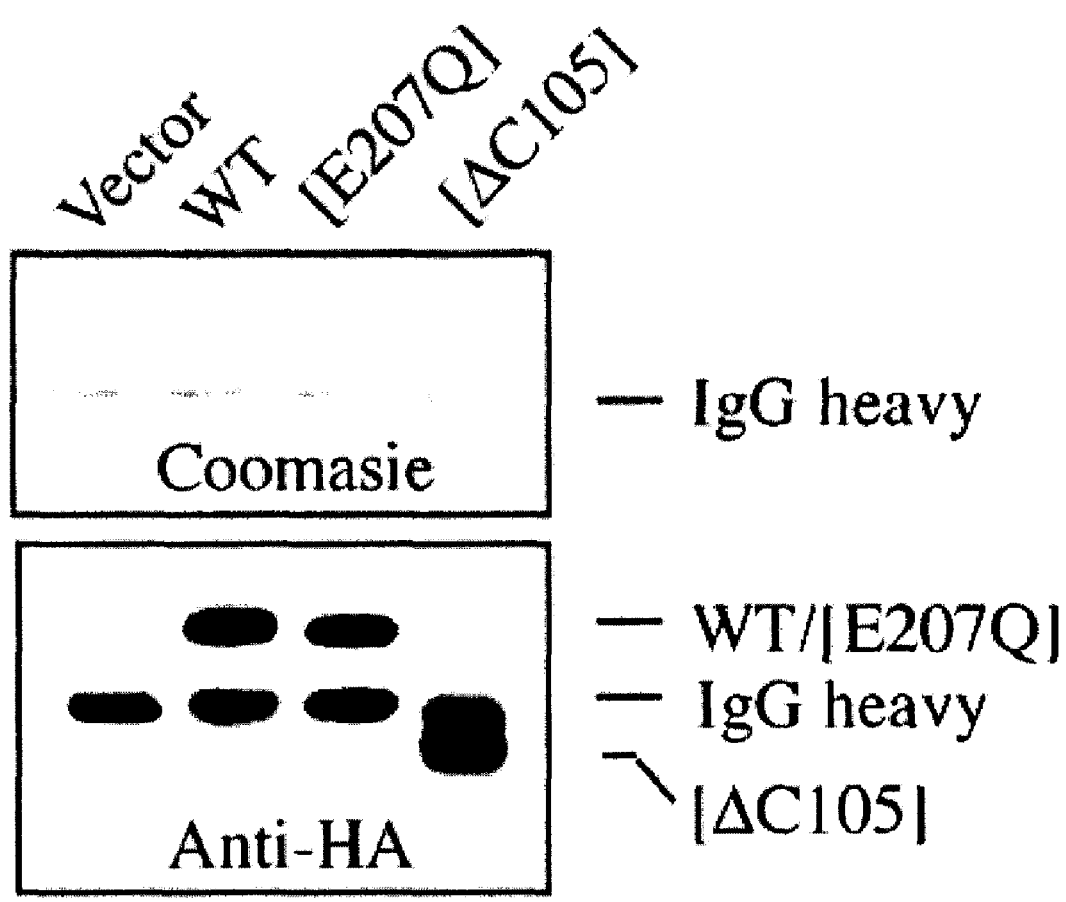
FIG. 17-FIG. 22 are photographs and graphs showing hydrolysis of ABA-GE by AtBG1 and changes of ABA level thereby.

The expressed proteins were immunopurified using anti-HA antibody (FIG. 17), and the immunopurified proteins were incubated with ABA-GE (APEX ORGANICS LTD.) in vitro in 100 mM citrate buffer (pH 5.5) at 37° C. for one and half hours. The reactants were separated by HPLC equipped with a specific solvent (40% methanol, 0.1 M acetic acid, 10 mg/l butyrate hydroxytoluene) packing column (RT 250-4 column, MERCK).

Figure 18:
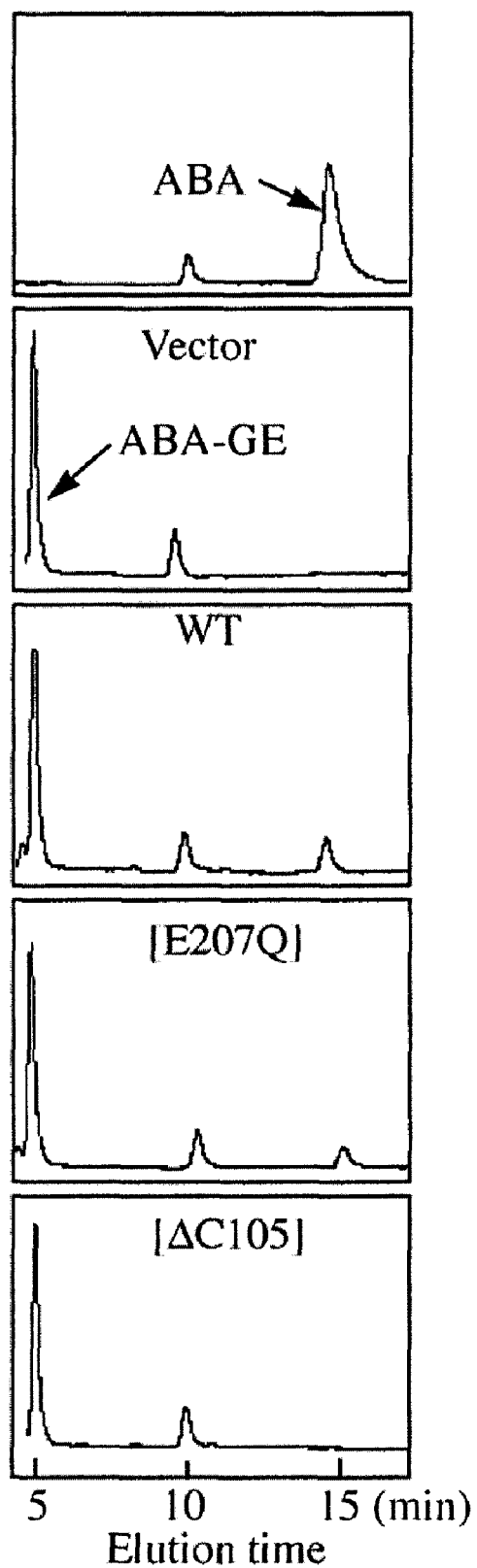

As a result, AtBG1:HA and AtBG1[E207Q]:HA displayed novel peaks at the position for ABA (FIG. 18). The ABA peaks were quantified by ELISA using an anti-ABA antibody (cannot recognize ABA-GE).

Figure 19:
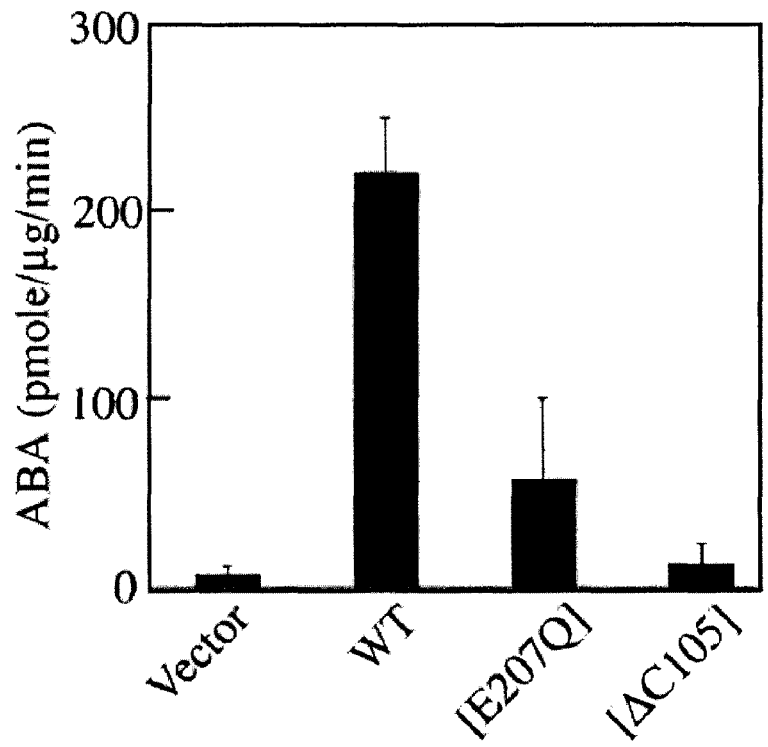

The amount of ABA released by AtBG1[E207Q]:HA was significantly reduced to 20% that of the wild type (FIG. 19), indicating that glutamic acid at position 207 is important for hydrolytic activity, similar to other β-glucosidases (Davies G. and Henrissat B., *Structure* 3: 853, 1995; Marana S. R. et al., *Biochim. Biophys. Acta* 1545: 41, 2001). However, neither AtBG1 [ΔC105]:HA nor the vector control displayed detectable levels of ABA generated from ABA-GE, which was consistent with the other result that ABA generation is reduced or inhibited in the 'mutant atbg1'. Taken together, these results indicate that AtBG1:HA hydrolyzes ABA-GE to form ABA.

<4-2> Investigation of the Level of ABA in Seeds

Seeds contain ABA more than any other parts of a plant. To verify the above results, the present inventors measured the levels of ABA in seeds of wild type, 'mutant atbg1' and 'rescued atbg1'.

A compound was extracted from seeds mashed by liquid nitrogen using 80% ethanol, and ABA peaks were obtained by HPLC equipped with C18 column (J. T. Baker). The ABA fractions were measured by ELISA using anti-ABA antibody (Agdia).

Figure 20:
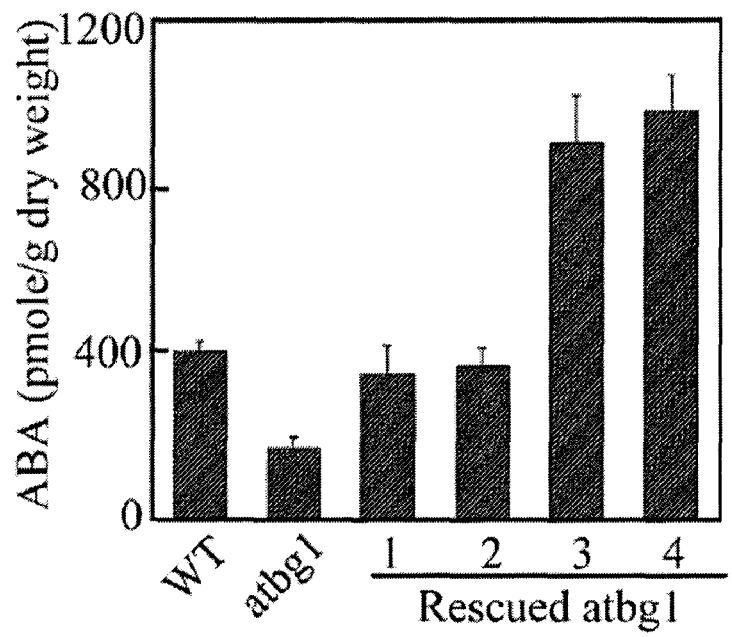
Figure 21:
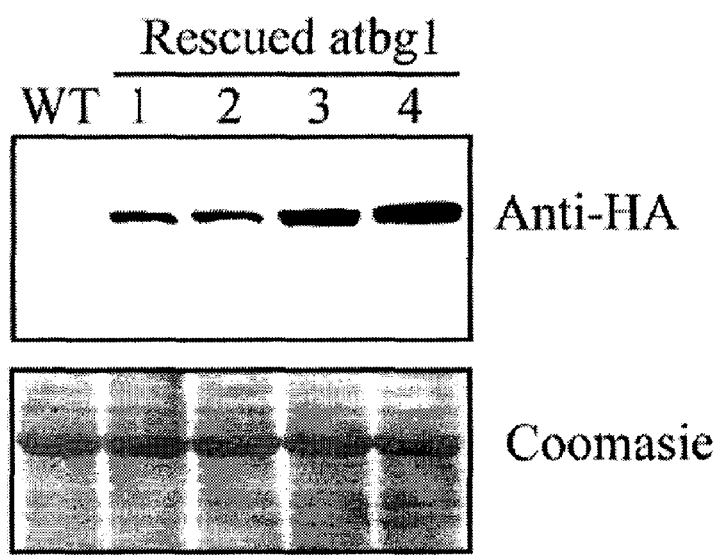

The ABA content in 'mutant atbg1' seeds was approximately 40% that of the wild-type (FIG. 20). In 'rescued atbg1' plant seeds, the ABA content ranged from 86% to 250% of the wild-type. That is, ABA content in 'mutant atbg1' seeds was very low, compared with that in wild type, but the ABA content in 'rescued atbg1' seeds was similar or double the content in wild type. The AtBG1:HA content in 'rescued atbg1' seeds was also quantified using anti-HA antibody (FIG. 21), resulting in the similar ABA level to that quantified by HPLC (FIG. 20). So, it was confirmed that ABA content is closely related to AtBG1 protein level.

<4-3> Investigation of Germination

Figure 22:
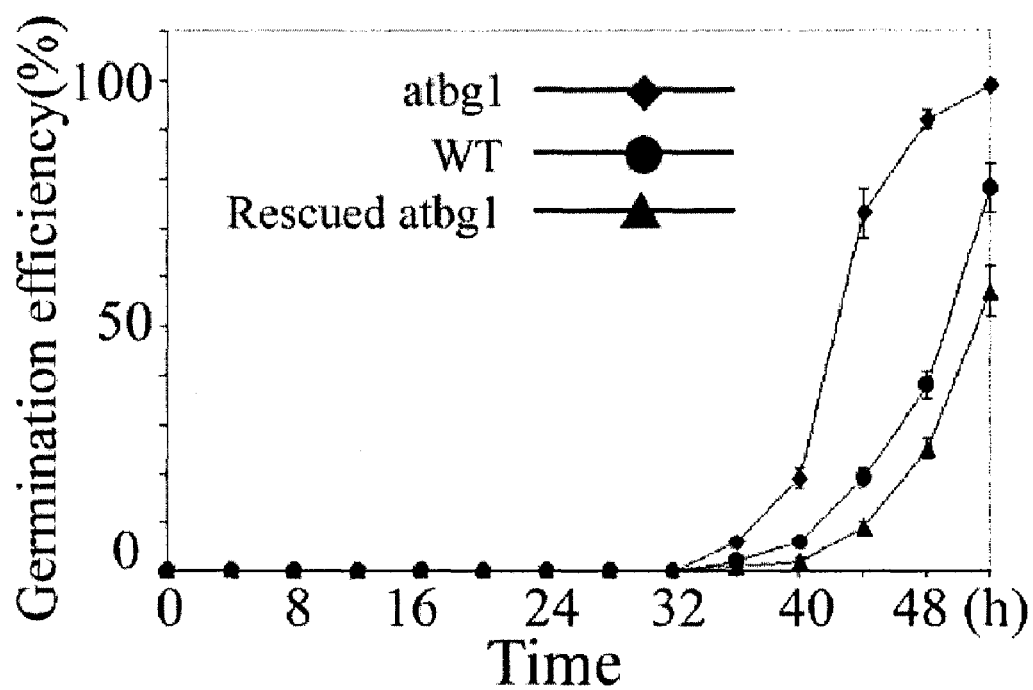

The present inventors examined whether the ABA content in seeds is related to germination. Precisely, germination assay was performed in wild type, 'mutant atbg1' and 'rescued atbg1'. As a result, germination was delayed in 'rescued atbg1', whereas the 'atbg1 mutant' germinated earlier, compared with wild type (FIG. 22). The results indicate that 'atbg1 mutant' contains lower level of ABA than that of wild type and AtBG1 protein which no more contains atbg1 mutant gene does not hydrolyze ABA-GE to form ABA even though there is a small amount of ABA contained.

Example 5

Confirmation of the Location of Cellular AtBG1 Using Fluorescent Microscope

<5-1> Observation of GFP-Labeled AtBG1 on Fluorescent Microscope

ABA-GE, an inert abscisic acid, localizes to the ER.

AtBG1 hydrolyzes ABA-GE to form ABA and harbors a sequence motif of REEL, which is similar to ER retention sequence KDEL, at C-terminal (Davies G. and B. Henrissat, *Structure* 3: 853, 1995). Based on that, the present inventors observed AtBG1 under fluorescent microscope to confirm whether AtBG1 also localizes to ER, like ABA-GE.

Figure 24:
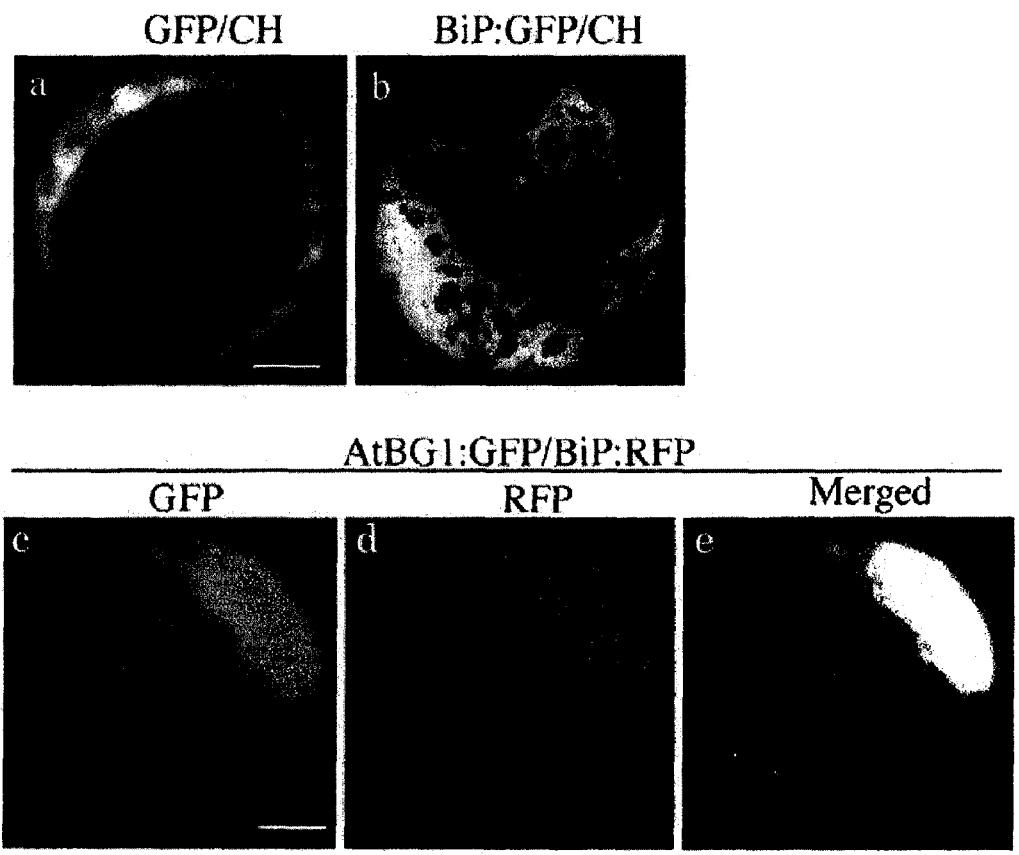

Particularly, *Arabidopsis thaliana* was transformed with GFP:AtBG1, a recombinant AtBG1 gene in which down stream of leader sequence was labeled with green fluorescence protein (GFP) and BiP:RFP, a recombinant BiP in which ER chaperone binding protein BiP (immunoglobulin binding protein) was labeled with red fluorescence protein (REP), followed by observation under fluorescent microscope (FIG. 24).

Figure 23:
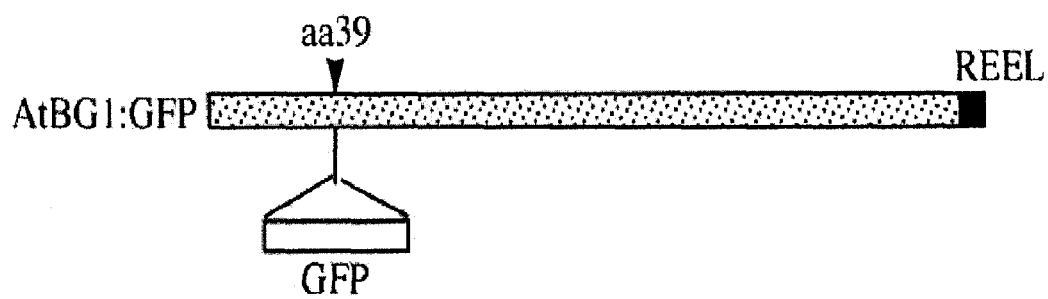
FIG. 23-FIG. 26 are photographs showing intracellular locations of AtBG1.

GFP:AtBG1 exhibited a multiple network pattern (panel c) implying the ER structure, while GFP only exhibited diffused pattern (FIG. 23, panel a). The GFP:AtBG1 pattern was closely overlapping that of BiP:REP (panel d), the ER chaperone binding protein (panel e) (Jin J. B., et al., *Plant Cell* 13: 1511, 2001). The results indicate that AtBG1 localizes to the ER along with BiP.

AtBG1:HA was examined immunohistochemically using the anti-HA antibody to confirm the result that AtBG1 localizes to the ER. As a result, AtBG1:HA displayed a characteristic ER specific network pattern closely overlapping that of BiP:RFP (FIG. 24).

<5-2> AtBG1 Glycosylation

To confirm the above result that AtBG1 localizes to ER, the present inventors examined AtBG1 glycosylation. Glycosylation of protein produces glycan and this glycan moiety of the protein localizing to the ER is sensitive to both endo-H and PNGase F, meaning the glycan moiety is easily digested by endo-H and PNGase F enzyme activities (Kuznetsov G. et al., *J. Biol. Chem.* 268: 2001, 1993). Tunicamycin is an inhibitor of the glycosylation.

Protein extract obtained from protoplasts of AtBG1:HA transfected plant and treated with endo-H and PNGase F (not treated with tunicamycin), protein extract obtained from protoplasts of tunicamycin treated *Arabidopsis thaliana* transformed with AtBG1 and protein extract obtained from protoplasts of tunicamycin-non-treated *Arabidopsis thaliana* transformed with AtBG1 were examined by blotting using anti-HA antibody.

Figure 25:
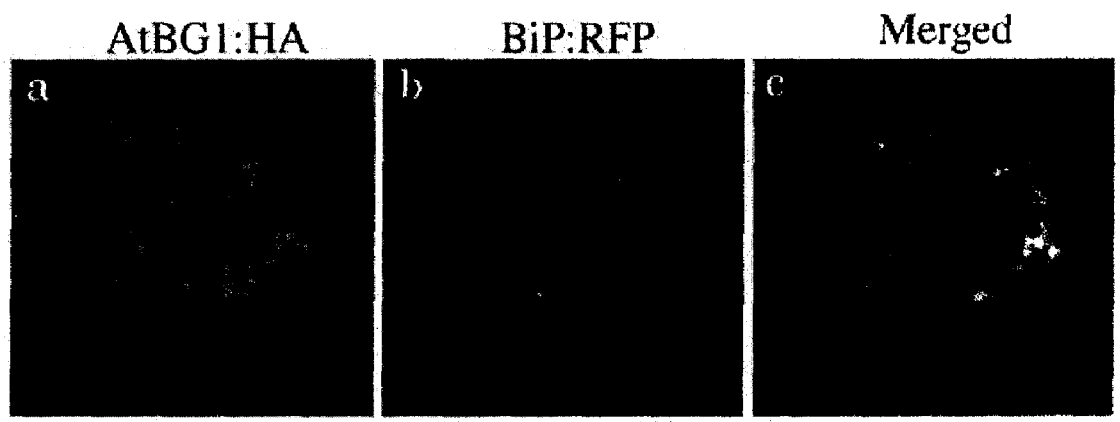
Figure 26:
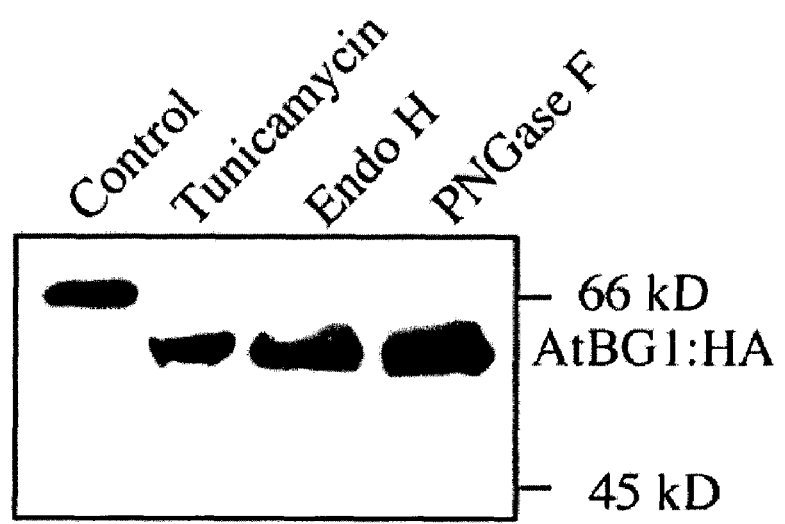

The size of AtBG1:HA obtained from tunicamycin-treated protoplasts was smaller than that obtained from tunicamycin-non-treated protoplasts, indicating that glycosylation did not occur by tunicamycin so that glycan was not produced. AtBG1:HA in which glycan moiety was digested with endo-H and PNGase F was the same size with tunicamycin-treated AtBG1:HA, which supports the above indication. That is, glycan moiety of AtBG1:HA is very sensitive to endo-H and PNGase F so as to by digestion with such enzymes, resulting in the same size with tunicamycin-treated AtBG1 (FIG. 25). The results suggest that AtBG1 localizes to ER.

Example 6

Figure 27:
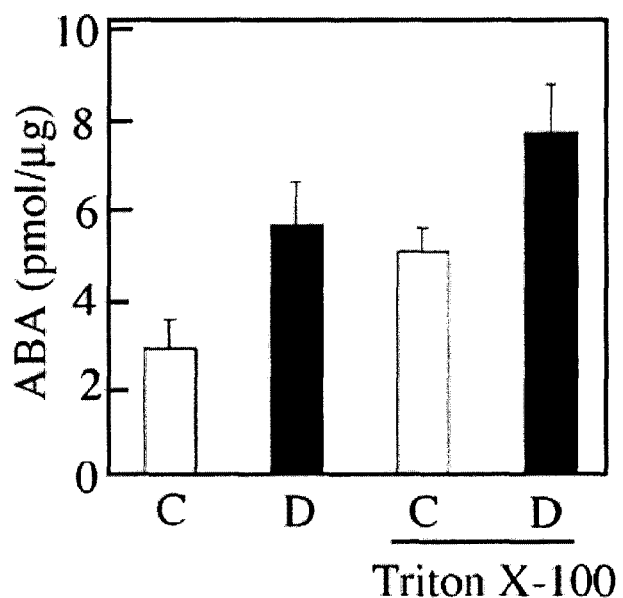
FIG. 27-FIG. 31 are graphs and photographs showing that ABA-GE hydrolyzing activity of AtBG1 in microsomes is enhanced by rapid polymerization of AtBG1 under dehydration condition.

ABA-GE Hydrolyzing Activity of AtBG1 by Dehydration Stress-Induced Polymerization To establish the cause of the substantial increase of ABA content in 'rescued atbg1' plants subjected to dehydration, the present inventors compared microsomes of 'rescued atbg1' plants subjected to dehydration under the condition of 30% relative humidity for 10 hours with those of 'rescued atbg1' plants grown under normal conditions for their ability to produce ABA from ABA-GE. Microsomes of plants were pulverized in homogenizer buffer (250 mM Sucrose 25 mM HEPES pH 7.0, 10 mM MgCl$_2$, 1 mM DTT), followed by centrifugation at 3,000 rpm for 5 minutes and at 14,000 for 5 minutes. The separated supernatants were ultracentrifuged at 100,000 g. ABA content was quantified by reacting the obtained microsomes in 100 mM citrate buffer (pH 5.5) and using ABA antibody containing ELISA kit (Agdia). As a result, microsomes from 'rescued atbg1' plants pretreated with dehydration exhibited a significant increase in ABA production, compared with control microsomes, grown under normal conditions (FIG. 27).

Figure 35:
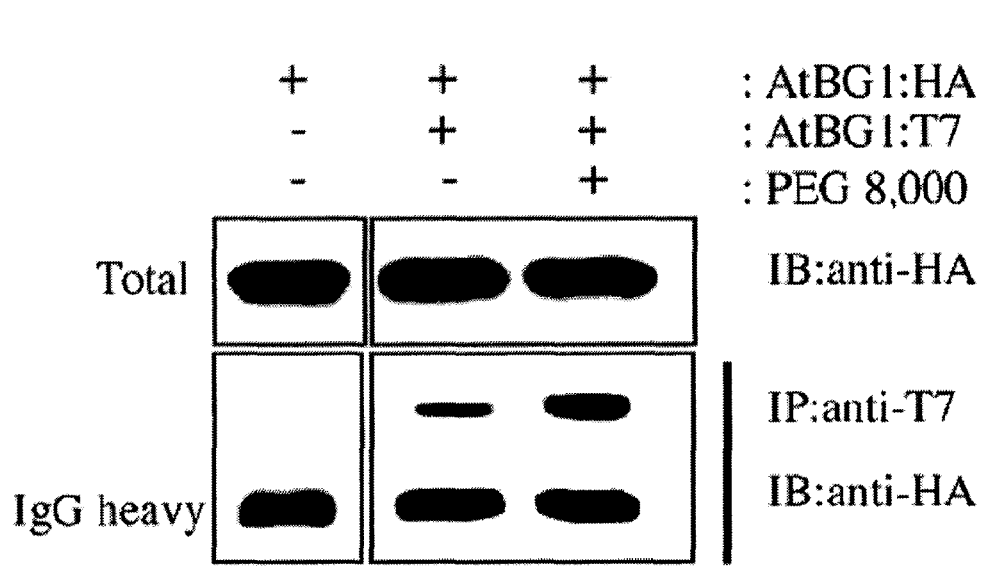
FIG. 35 is a photograph showing the result of immunoprecipitation, using anti-T7 antibody, followed by western blotting using anti-HA antibody, of protein extracts obtained from protoplasts of transgenic plants having osmotic stress with PEG8000.

The present inventors also investigated the mechanism by which dehydration stress activates AtBG1. A previous study shows that polymerized forms of β-glucosidases have higher enzyme activity than dimer forms (Kim and Kim, 1998). Thus, the present inventors investigated whether the mechanism by which dehydration stress activates AtBG1 is attributed to AtBG1 polymerization. Protein extracts were prepared from protoplasts co-transformed with two differently tagged forms of AtBG1, AtBG1:HA and AtBG1:T7, according to the same method as described in the above Example, and used for co-immunoprecipitation with anti-T7 antibody. Immunoprecipitates were analyzed by Western blotting using anti-HA antibody to investigate the interaction between AtBG1 molecules. As a result, HA-tagged AtBG1 was detected in the precipitate immunoprecipitated with T7-antibody (FIG. 35). Furthermore, the amount of HA-tagged AtBG1 in the precipitate was increased by approximately 3-fold upon treatment of protoplasts with 10% PEG 8000, a chemical that induces dehydration stress, for 12 hours (measured by densitometry software, FIG. 35). Therefore, the present inventors concluded that AtBG1 undergoes homomeric interactions, which are enhanced under conditions of dehydration stress.

To further address this possibility, leaves of 'rescued atbg1' plants in the presence or absence of dehydration stress were crushed in homogenizing buffer (50 mM sodium phosphate, pH 7.0, 0.15 M NaCl, 0.02% NaN$_3$, 0.1% Triton X-100), followed by centrifugation at 14,000 g for 5 minutes. From the supernatant, protein extract was obtained. The protein extract was loaded on Sephacryl S-300 high-resolution column (Amersham) and protein fractions were obtained by using elution buffer (50 mM sodium phosphate, pH 7.0, 0.15 M NaCl, 0.02% NaN$_3$) at the flow speed of 0.5 ml/min per 3.0 ml fraction volume. The fractions were analyzed by Western blotting using anti-HA antibody.

Figure 28:
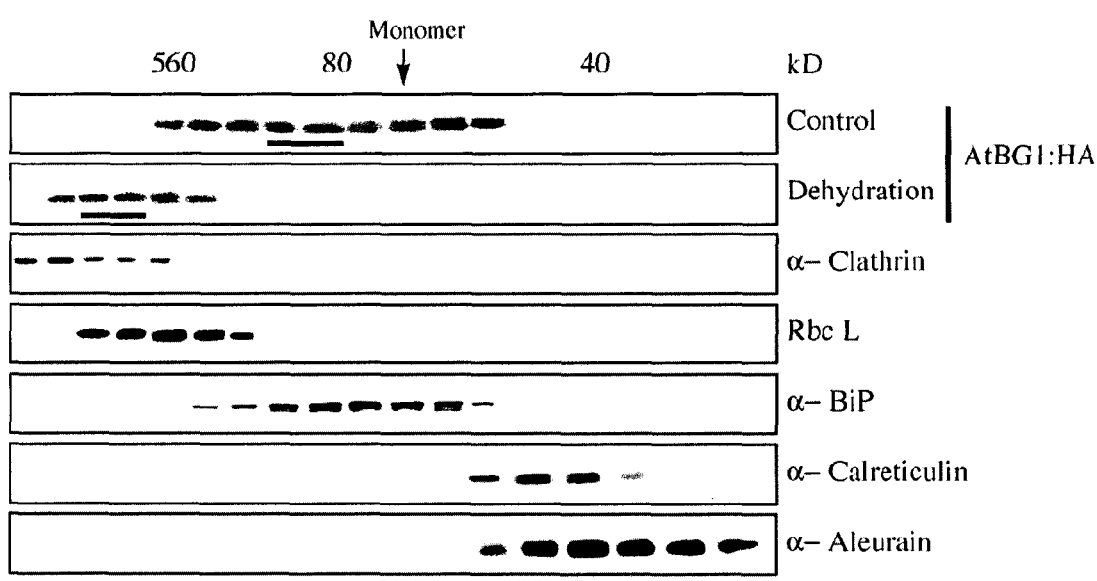
Figure 30:
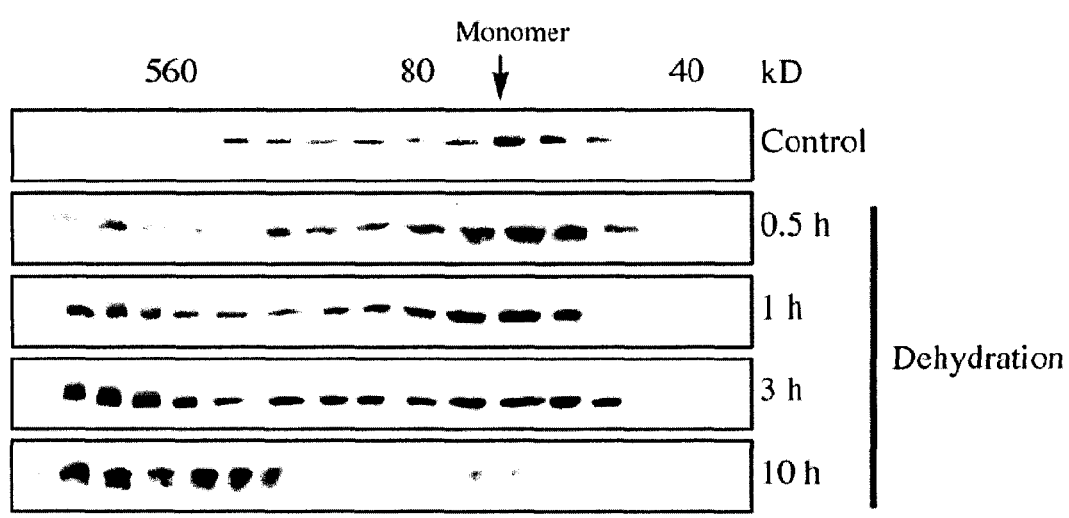

As a result, AtBH1:HA from 'rescued atbg1' not subject to dehydration stress existed primarily as monomers with a small proportion of higher molecular weight forms (FIG. 30). In contrast, AtBG1:HA from 'rescued atbg1' subject to dehydration stress existed as higher molecular weight forms with almost no dimers or monomers (FIG. 28). The molecular weight of the main peak of AtBG1 in dehydration-treated plants corresponded to over 600 kDA, which is equivalent to AtBG1 10-mer. The results indicate that dehydration stress induces polymerization of AtBG1.

Figure 29:
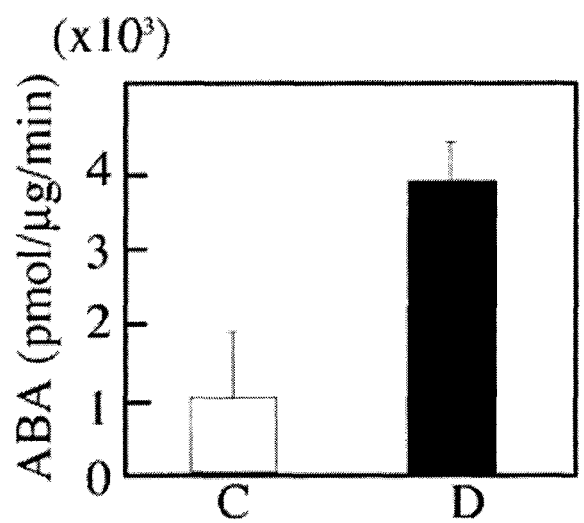

The enzyme activities of high and low molecular weight forms of AtBG1 were compared. High and low molecular weight fractions obtained from gel filtration using the same column as used in the above Example were immunoprecipitated using anti-HA antibody, followed by quantification of ABA content by ELISA. High molecular weight forms exhibited 4-fold higher AtBG1 activity (FIG. 29), which was consistent with the finding that microsomes from dehydration-stressed plants have enhanced ABA-GE hydrolyzing activity (FIG. 27).

Next, the present inventors measured the speed of AtBG1 assembly into higher molecular forms upon dehydration stress. Protein extract was prepared from 'rescued atbg1' plants subjected to dehydration at various time-points of 30 minutes, one hour and three hours upon dehydration stress and fractionated by gel filtration chromatography, which were examined by Western blotting using anti-HA antibody.

Figure 31:
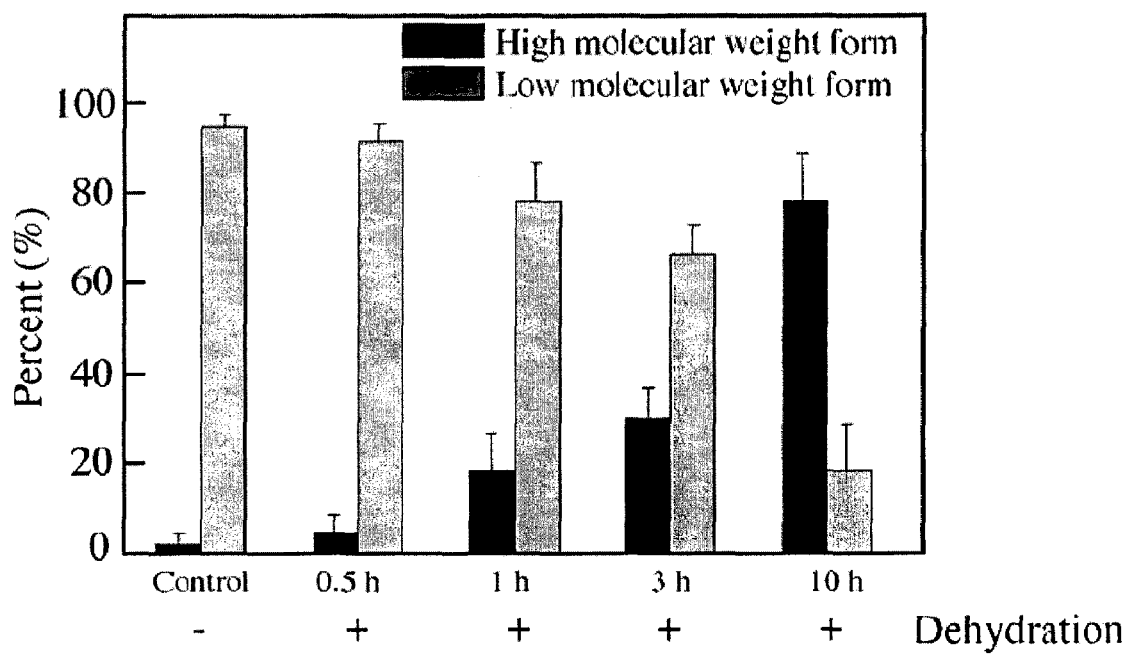

As a result, the higher molecular weight forms appeared 30 minutes after dehydration and gradually increased over time (FIG. 30 and FIG. 31). At 10 hours after dehydration stress, over 80% higher molecular weight AtBG1 was observed (FIG. 30 and FIG. 31). Thus, the assembly of AtBG1 into higher molecular weight forms upon dehydration stress is rapid and extensive.

Example 7

Polymerization Pattern of AtBG1 into Higher Molecular Weight Forms

The water status in plants changes constantly within a day under normal growth conditions. Transpiration rates reach the highest levels at midday under brighter sunlight, which periodically lowers water potential or leads to transient water deficit at midday. Accordingly, the present inventors hypothesize that the ABA levels in leaves undergo diurnal fluctuation. Specifically, a higher cellular ABA level is observed at midday when the sunlight is brighter, and lower ABA level at night.

To confirm the theory, the present inventors measured the ABA levels in leaves of wild-type and 'rescued atbg1' plants grown under normal conditions every 6 hours.

Figure 32:
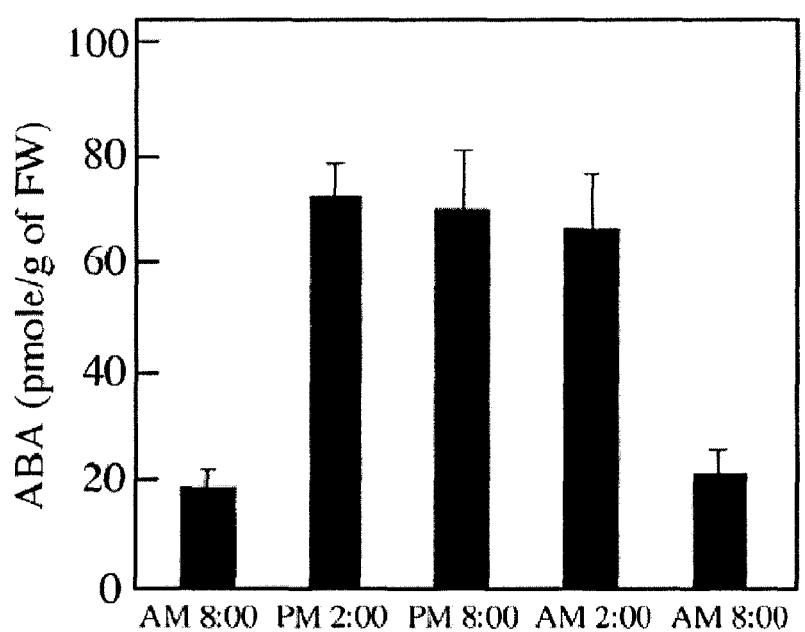
FIG. 32-FIG. 34 are photographs and graphs showing the polymerization of AtBG1 into high molecular weight forms in proportion to the level of ABA.

Particularly, upper parts of leaves were cut and dipped in 80% methanol and crushed by mortar and extraction was performed at 4° C. for 3 hours and then separated supernatant was passed through C-18 column (BMS), followed by freeze-drying. The resultant was dissolved in TBS buffer (Agdia) and the ABA level was measured by ELISA. As a result, the ABA levels of leaves displayed diurnal fluctuation within a given day, with the lowest and highest concentrations at 8:00 AM and 2:00 PM in 'rescued atbg1' plants, respectively (FIG. 32). The wild type plants showed a similar ABA pattern but with slightly lower levels.

Figure 36:
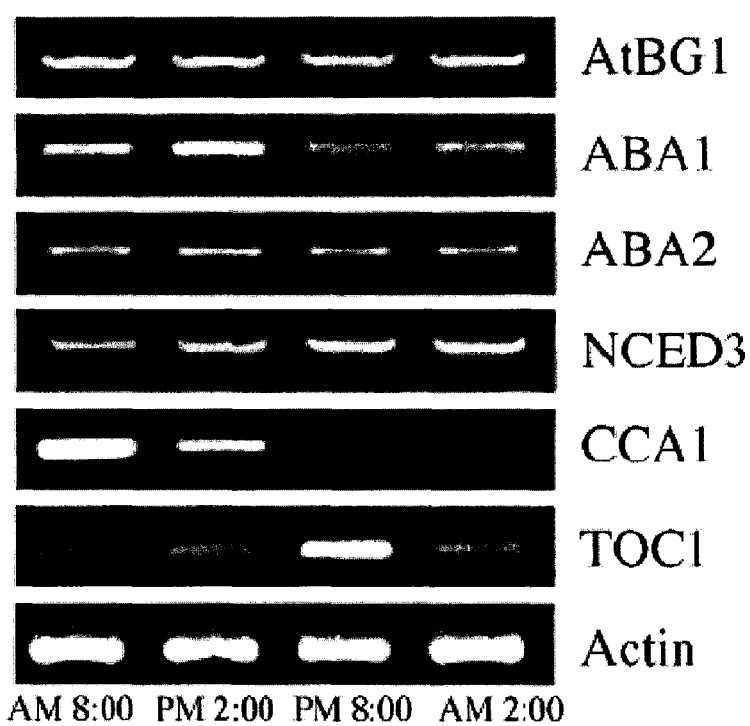
FIG. 36-FIG. 38 are photographs and graphs showing the gene expressions involved in de novo ABA biosynthesis pathway.

To investigate the cause of this increase in diurnal fluctuation of ABA, the present inventors measured the levels of AtBG1 transcripts as well as AtABA1, AtABA2 and AtNCED3 transcripts, which are critical for de novo ABA biosynthesis in wild type plants at various time-points within a day (FIG. 36). RT-PCR was performed with 10 mg of total RNA and 10 ng of each primer (total reaction volume was 100 ml, RT reaction mixture 5 ml) at 94° C. for 30 seconds, at 50° C. for 30 seconds and at 72° C. for 30 seconds and the number of cycles were determined from 15 to 35 according to gene levels. Gene specific primers represented by SEQ. ID. No 11 and No 12 (AtBG1), No 13 and No 14 (ABA1), No 15 and No 16 (ABA2), No 17 and No 18 (NCED3), No 19 and No 20 (positive control CCA1), No 21 and No 22 (positive control TOC1), and No 23 and No 24 (negative control actin) were used for the RT-PCR.

Figure 37:
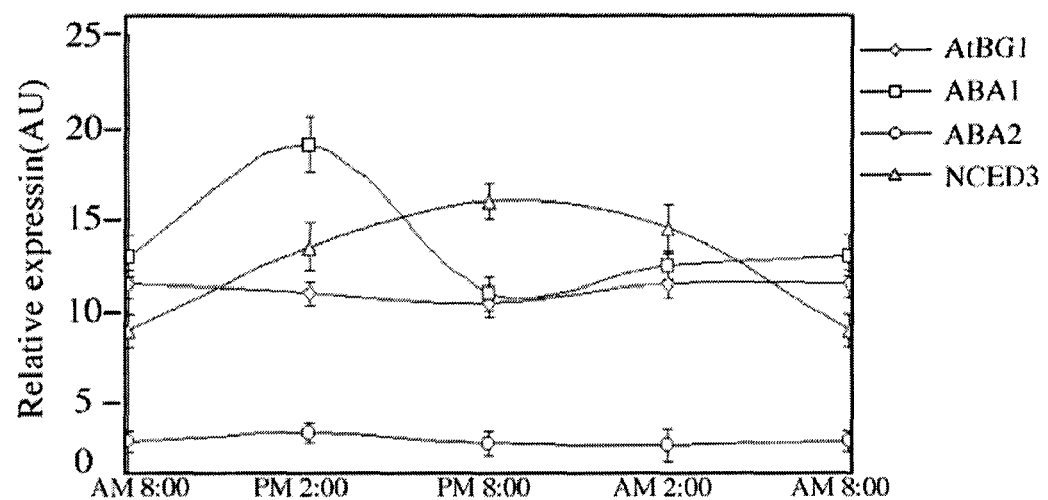

From the RT-PCR, it was confirmed that the AtBG1 and AtABA2 mRNA levels remained constant throughout a given day under the normal growth conditions employed (FIG. 36-FIG. 38), indicating that plants do not experienced dehydration stress under these conditions. And also, the higher ABA content was not due to enhanced expression of AtBG1. The level of AtABA1 transcript fluctuated with an approximate 1.7-fold increase at 2:00 PM (FIG. 36 and FIG. 37). In addition, AtNCED3 mRNA expression was 1.8-fold increased at 8:00 PM, and remained elevated until 2:00 AM but returned to the basal level at 8:00 AM. The above results indicate that both AtABA1 and AtNCED3 mRNA levels display diurnal fluctuation. However, the oscillation patterns of these mRNA levels did not overlap with that of ABA levels. Moreover the degree of fluctuation of mRNA levels was less than 2-fold.

As described above, the expression pattern of de novo biosynthesis involved gene was different from that of ABA, which indicates that de novo synthesis of ABA may not contribute to the rise in ABA levels at midday.

Figure 38:
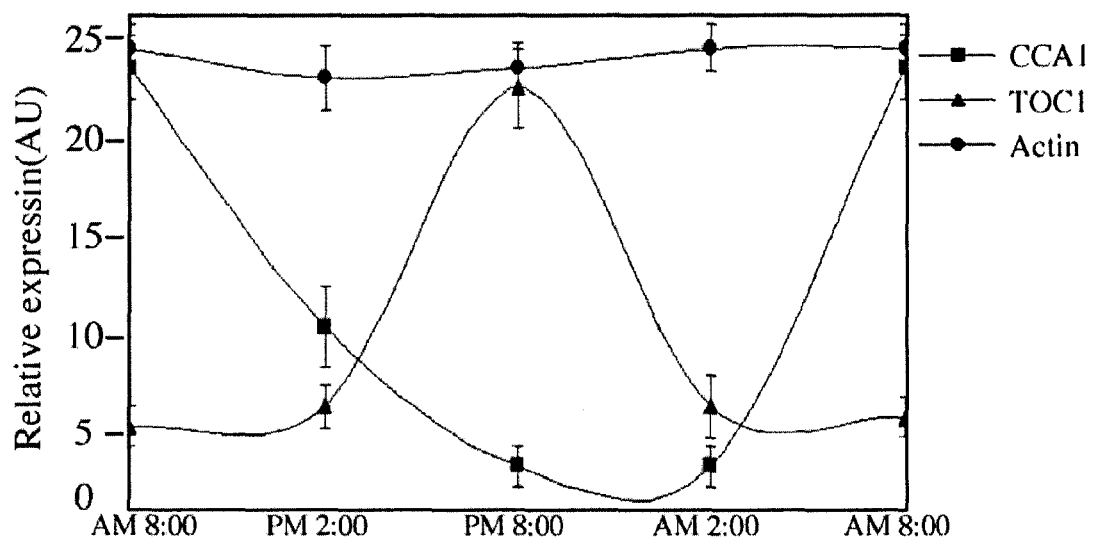

CCA1 and TOC1 transcript concentrations were examined as positive controls for circadian rhythm, and actin was used as a negative control for circadian rhythm (Wang and Tobin, 1998; Strayer et al., 2000) (FIG. 36 and FIG. 38).

The present inventors, next, examined whether AtBG1 contributes to the diurnal fluctuation of ABA levels by the polymerization-mediated activation of AtBG1.

Figure 33:
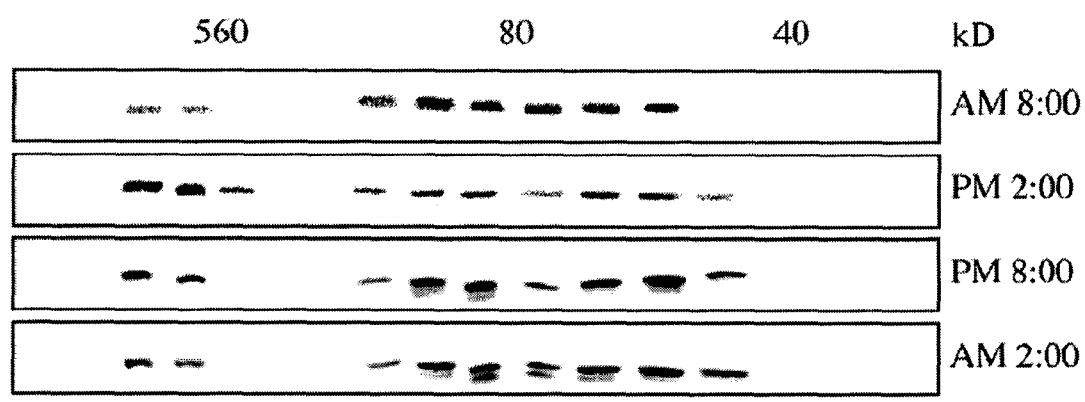
Figure 34:
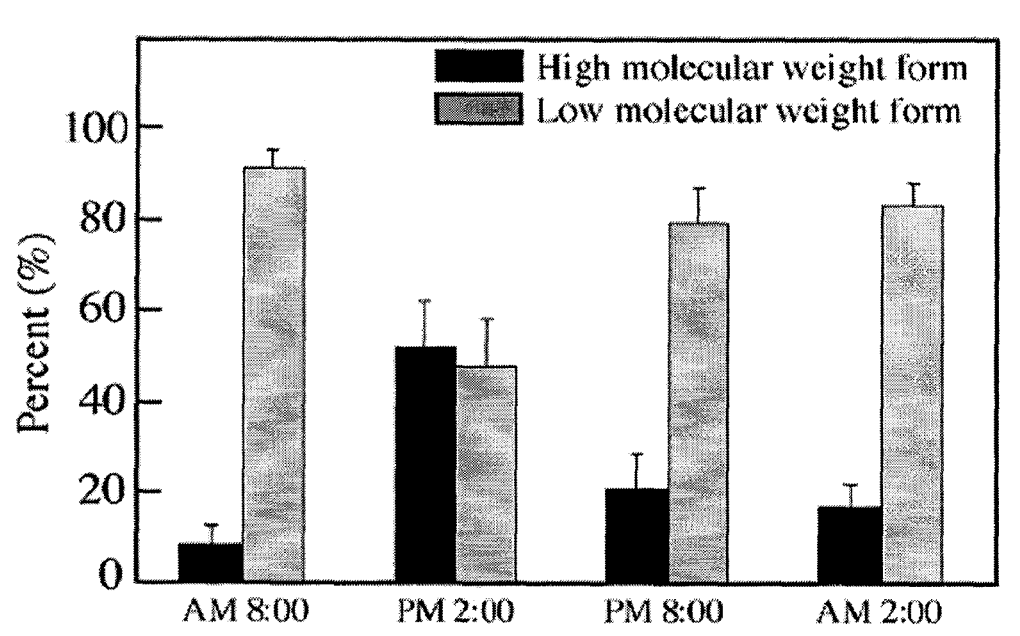

Total protein extracts obtained from 'rescued atbg1' plants grown under normal conditions at different time-points were fractionated using a gel filtration column, and analyzed by Western blotting using anti-HA antibody. As a result, higher molecular weight AtBG1 showed diurnal fluctuation (FIG. 33 and FIG. 34). Levels peaked at 2:00 PM, followed by a rapid decline, and were lowest at 8:00 AM. At 2:00 PM, approximately half the total AtBG1 existed in the higher molecular weight forms, whereas at 8:00 AM, less than 10% high molecular weight AtBG1 was observed. The concentration of high molecular weight AtBG1 correlated significantly with the increase in ABA content in leaf tissues during the day, strongly suggesting that the polymerization-mediated activation of AtBG1 is responsible for the increased ABA levels during diurnal fluctuation.

INDUSTRIAL APPLICABILITY

As explained hereinbefore, the transgenic plant harboring AtBG1 gene of the present invention can greatly contribute to the increase of agricultural production since the AtBG1 protein expressed in the transgenic plant activates abscisic acid (ABA) and thus increase resistance to various environmental stresses.

SEQUENCE LIST TEXT

SEQ. ID. No 1 and No 2 are primer sequences used for the isolation of AtBG1, an *Arabidopsis thaliana* gene, from subtraction cDNA library, SEQ. ID. No 3 is a nucleotide sequence of AtBG1 gene, SEQ. ID. No 4 and No 5 are primer sequences used for obtaining Gluc (AF082157) and psr3.1 (U72153) from entire cDNA library, SEQ. ID. No 6, No 7 and No 8 are primer sequences used for the confirmation of a T-DNA insertion in AtBG1 gene, SEQ. ID. No 9 and No 10 are primer sequences used for obtaining AtBG1 upstream 1.7 kb region, SEQ. ID. No 11 and No 12 are primer sequences specific to AtBG1, SEQ. ID. No 13 and No 14 are primer sequences specific to ABA1, SEQ. ID. No 15 and No 16 are primer sequences specific to ABA2, SEQ. ID. No 17 and No 18 are primer sequences specific to NCED3, SEQ. ID. No 19 and No 20 are primer sequences specific to positive control CCA1, SEQ. ID. No 21 and No 22 are primer sequences specific to positive control TOC1, SEQ. ID. No 23 and No 24 are primer sequences specific to negative control actin, SEQ. ID. No 25 and No 26 are primer sequences specific to AtBG1.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A transgenic plant containing an insertion of an AtBG1 gene having the nucleotide sequence of SEQ ID NO: 3, wherein,
   the transgenic plant has enhanced resistance to environmental stress; and
   the AtBG1 gene is an *Arabidopsis thaliana* gene encoding a β-glucosidase homolog,
   wherein,
   the environmental stress is selected from the group consisting of dehydration, salt damage, low temperature and osmotic shock.

2. An offspring or a clone of the transgenic plant of claim 1, wherein the offspring or the clone has the AtBG1 gene having the nucleotide sequence of SEQ ID NO: 3.

3. A seed, a fruit, an ear, a tuber, a tuberous root, a tree, a callus or a protoplast of the transgenic plant of claim 1, wherein the seed, the fruit, the ear, the tuber, the tuberous root, the tree, the callus or the protoplast has the AtBG1 gene having the nucleotide sequence of SEQ ID NO: 3.

4. A method for generating a transgenic plant having resistance to environmental stress comprising:
   i) inserting an AtBG1 gene having the nucleotide sequence of SEQ ID NO: 3 into plant cells; and
   ii) redifferentiating the plant cells by tissue culture wherein,
   the AtBG1 gene is an *Arabidopsis thaliana* gene encoding a β-glucosidase homolog; and the environmental stress is selected from the group consisting of dehydration, salt damage, low temperature and osmotic shock.

5. A method for providing stress-resistance to a plant comprising:
   i) inserting an AtBG1 gene having the nucleotide sequence of SEQ ID NO: 3 into plant cells; and
   ii) preparing a transgenic plant by redifferentiating the plant cells by tissue culture, thereby increasing the expression of the AtBG1 gene,
   wherein,
   the AtBG1 gene is an *Arabidopsis thaliana* gene encoding a β-glucosidase homolog; and the stress is selected from the group consisting of dehydration, salt damage, low temperature and osmotic shock.

6. The method as set forth in claim 5, wherein the AtGB1 gene provides stress-resistance to a plant by increasing abscisic acid (ABA) content through hydrolysis of ABA glucose ester (ABA-GE).

7. The method as set forth in claim 6, wherein the hydrolysis of ABA-GE is catalyzed by AtBG1 polymerization.

* * * * *

SEQUENCE LISTING

```
<160> NUMBER OF SEQ ID NOS: 26

<210> SEQ ID NO 1
<211> LENGTH: 22
<212> TYPE: DNA
<213> ORGANISM: Artificial Sequence
<220> FEATURE:
<223> OTHER INFORMATION: PRIMER 1

<400> SEQUENCE: 1
atggtgaggt tcgagaaggt tc                                              22

<210> SEQ ID NO 2
<211> LENGTH: 22
<212> TYPE: DNA
<213> ORGANISM: Artificial Sequence
<220> FEATURE:
<223> OTHER INFORMATION: PRIMER 2

<400> SEQUENCE: 2
ctagagttct tccctcagct tg                                              22

<210> SEQ ID NO 3
<211> LENGTH: 1587
<212> TYPE: DNA
<213> ORGANISM: Artificial Sequence
<220> FEATURE:
<223> OTHER INFORMATION: Arabidopsis thaliana

<400> SEQUENCE: 3
atggtgaggt tcgagaaggt tcatttagtg ttagggttag ctctggttct aactctggtc      60
ggagctccga ccaaagccca aggacctgtt tgcggtgcag gcctgcctga caaatttagc     120
agattaaact tccctgaagg cttcatttgg ggaaccgcaa cagcagcatt tcaggttgaa     180
ggagctgtta atgaaggttg cagaggtcca agcatgtggg atactttcac taagaagttc     240
ccacatagat gtgaaaatca taacgctgat gttgctgtgg atttctatca tcgttacaag     300
gaagatatcc agttgatgaa agaccttaac actgatgctt ttagactttc tattgcgtgg     360
cccagaatat tccccatgg aaggatgtct aagggaataa acaaagtggg agtccaattc     420
taccacgacc tcatcgatga gcttctcaaa aacaatataa taccattagt tacagtcttt     480
cattgggata ctccccaaga cttggaagat gaatatggtg gtttcttaag tggtcgcatc     540
gtgcaagatt ttaccgaata tgcgaatttc actttccacg aatatggaca caaagtgaaa     600
```

-continued

| | |
|---|---|
| cattggatca catttaacga gccatgggtg tttagtcgtg ccggttacga caacggaaag | 660 |
| aaagctccgg gacgttgttc gccgtacatc cccggttatg gacagcattg tcaggatggg | 720 |
| cggtctggat acgaagctta tcaagtcagt cacaacttac tcttgtcgca tgcttacgct | 780 |
| gttgacgcat tcagaaactg caaacagtgt gctggaggta aaattggaat tgcacacagt | 840 |
| ccagcttggt tcgaaccaca agaccttgag catgttggag gttccattga acgtgtgctt | 900 |
| gatttcatcc taggatggca tttggctcca acaacttatg gagattatcc acaatcgatg | 960 |
| aaggatcgtg tcggtcatag attgccaaaa ttcacagaag ctgagaagaa gttgctaaag | 1020 |
| ggttctacag attacgtagg aatgaattac tatacttcag tgtttgcaaa agaaattagc | 1080 |
| cctgatccta agagtccgag ttggacgact gattctcttg ttgattggga tagcaagagt | 1140 |
| gtggatggat acaaaattgg tagcaagccg tttaatggta aactggatgt gtattcaaaa | 1200 |
| ggtttgagat accttttgaa gtatattaag gataactatg gcgacccaga agttatcatt | 1260 |
| gccgagaatg gatacggaga agaccttgga gagaagcaca atgacgtaaa ctttgggaca | 1320 |
| caagatcaca acagaaaata ttatatccaa aggcatctct tgagtatgca cgacgccatt | 1380 |
| tgcaaggaca aagtgaacgt tacgggatac tttgtgtggt ctttgatgga caactttgag | 1440 |
| tggcaagatg ggtacaaggc gaggttcgga ctttactaca tcgatttcca gaacaacttg | 1500 |
| acccgtcacc aaaagtttc gggcaaatgg tattccgaat tcctcaaacc acagtttcca | 1560 |
| acctccaagc tgagggaaga actctag | 1587 |

```
<210> SEQ ID NO 4
<211> LENGTH: 22
<212> TYPE: DNA
<213> ORGANISM: Artificial Sequence
<220> FEATURE:
<223> OTHER INFORMATION: PRIMER 3

<400> SEQUENCE: 4
atggtgaggt tcgagaaggt tc                                              22

<210> SEQ ID NO 5
<211> LENGTH: 22
<212> TYPE: DNA
<213> ORGANISM: Artificial Sequence
<220> FEATURE:
<223> OTHER INFORMATION: PRIMER 4

<400> SEQUENCE: 5
ctagagttct ccctcagct tg                                               22

<210> SEQ ID NO 6
<211> LENGTH: 22
<212> TYPE: DNA
<213> ORGANISM: Artificial Sequence
<220> FEATURE:
<223> OTHER INFORMATION: PRIMER 5

<400> SEQUENCE: 6
gcgtggaccg cttgctgcaa ct                                              22

<210> SEQ ID NO 7
<211> LENGTH: 21
<212> TYPE: DNA
<213> ORGANISM: Artificial Sequence
<220> FEATURE:
<223> OTHER INFORMATION: PRIMER 6
```

```
<400> SEQUENCE: 7
tggaattgca cacagtccag c                                              21

<210> SEQ ID NO 8
<211> LENGTH: 23
<212> TYPE: DNA
<213> ORGANISM: Artificial Sequence
<220> FEATURE:
<223> OTHER INFORMATION: PRIMER 7

<400> SEQUENCE: 8
gcttctctcc aaggtcttct ccg                                            23

<210> SEQ ID NO 9
<211> LENGTH: 25
<212> TYPE: DNA
<213> ORGANISM: Artificial Sequence
<220> FEATURE:
<223> OTHER INFORMATION: AtBG1 promoter primer

<400> SEQUENCE: 9
gacgcaatac gaaagccaat aagtg                                          25

<210> SEQ ID NO 10
<211> LENGTH: 20
<212> TYPE: DNA
<213> ORGANISM: Artificial Sequence
<220> FEATURE:
<223> OTHER INFORMATION: AtBG1 promoter primer

<400> SEQUENCE: 10
tattgggtgg tctctctctc                                                20

<210> SEQ ID NO 11
<211> LENGTH: 22
<212> TYPE: DNA
<213> ORGANISM: Artificial Sequence
<220> FEATURE:
<223> OTHER INFORMATION: AtBG1 primer

<400> SEQUENCE: 11
atggtgaggt tcgagaaggt tc                                             22

<210> SEQ ID NO 12
<211> LENGTH: 21
<212> TYPE: DNA
<213> ORGANISM: Artificial Sequence
<220> FEATURE:
<223> OTHER INFORMATION: AtBG1 primer

<400> SEQUENCE: 12
ctcgttaaat gtgatccaat g                                              21

<210> SEQ ID NO 13
<211> LENGTH: 21
<212> TYPE: DNA
<213> ORGANISM: Artificial Sequence
<220> FEATURE:
<223> OTHER INFORMATION: ABA1 primer

<400> SEQUENCE: 13
atgggttcaa ctccgttttg c                                              21
```

```
<210> SEQ ID NO 14
<211> LENGTH: 22
<212> TYPE: DNA
<213> ORGANISM: Artificial Sequence
<220> FEATURE:
<223> OTHER INFORMATION: ABA1 primer

<400> SEQUENCE: 14
cataccaagt accagagata cc                                              22

<210> SEQ ID NO 15
<211> LENGTH: 26
<212> TYPE: DNA
<213> ORGANISM: Artificial Sequence
<220> FEATURE:
<223> OTHER INFORMATION: ABA2 primer

<400> SEQUENCE: 15
atgtcaacga acactgaatc ttcttc                                          26

<210> SEQ ID NO 16
<211> LENGTH: 22
<212> TYPE: DNA
<213> ORGANISM: Artificial Sequence
<220> FEATURE:
<223> OTHER INFORMATION: ABA2 primer

<400> SEQUENCE: 16
gcatgcttgg aaccaacata ag                                              22

<210> SEQ ID NO 17
<211> LENGTH: 20
<212> TYPE: DNA
<213> ORGANISM: Artificial Sequence
<220> FEATURE:
<223> OTHER INFORMATION: NCED3 primer

<400> SEQUENCE: 17
atggcttctt tcacggcaac                                                 20

<210> SEQ ID NO 18
<211> LENGTH: 18
<212> TYPE: DNA
<213> ORGANISM: Artificial Sequence
<220> FEATURE:
<223> OTHER INFORMATION: NCED3 primer

<400> SEQUENCE: 18
gtctccgtcg aagaagtg                                                   18

<210> SEQ ID NO 19
<211> LENGTH: 20
<212> TYPE: DNA
<213> ORGANISM: Artificial Sequence
<220> FEATURE:
<223> OTHER INFORMATION: CCA1 primer

<400> SEQUENCE: 19
tatcgaatcc aagctgattt                                                 20

<210> SEQ ID NO 20
<211> LENGTH: 19
<212> TYPE: DNA
<213> ORGANISM: Artificial Sequence
<220> FEATURE:
<223> OTHER INFORMATION: CCA1 primer
```

```
<400> SEQUENCE: 20
tttccagaga ttttgcatt                                                 19

<210> SEQ ID NO 21
<211> LENGTH: 20
<212> TYPE: DNA
<213> ORGANISM: Artificial Sequence
<220> FEATURE:
<223> OTHER INFORMATION: TOC1 primer

<400> SEQUENCE: 21
gctaggactt gctgagaaga                                                20

<210> SEQ ID NO 22
<211> LENGTH: 20
<212> TYPE: DNA
<213> ORGANISM: Artificial Sequence
<220> FEATURE:
<223> OTHER INFORMATION: TOC1 primer

<400> SEQUENCE: 22
tccctctact tctgtgtgct                                                20

<210> SEQ ID NO 23
<211> LENGTH: 24
<212> TYPE: DNA
<213> ORGANISM: Artificial Sequence
<220> FEATURE:
<223> OTHER INFORMATION: actin primer

<400> SEQUENCE: 23
aatcagatgt ggatctctaa ggca                                           24

<210> SEQ ID NO 24
<211> LENGTH: 24
<212> TYPE: DNA
<213> ORGANISM: Artificial Sequence
<220> FEATURE:
<223> OTHER INFORMATION: actin primer

<400> SEQUENCE: 24
tccgagtttg aagaggctac aaac                                           24

<210> SEQ ID NO 25
<211> LENGTH: 26
<212> TYPE: DNA
<213> ORGANISM: Artificial Sequence
<220> FEATURE:
<223> OTHER INFORMATION: AtBG1 primer

<400> SEQUENCE: 25
ttactatact tcagtgtttg caaaag                                         26

<210> SEQ ID NO 26
<211> LENGTH: 22
<212> TYPE: DNA
<213> ORGANISM: Artificial Sequence
<220> FEATURE:
<223> OTHER INFORMATION: AtBG1 primer

<400> SEQUENCE: 26
ctagagttct tccctcagct tg                                             22
```